(12) United States Patent
Cosman et al.

(10) Patent No.: US 9,956,032 B1
(45) Date of Patent: May 1, 2018

(54) ELECTROSURGICAL GENERATOR

(71) Applicant: COSMAN INSTRUMENTS, LLC, Burlington, MA (US)

(72) Inventors: Eric R. Cosman, Belmont, MA (US); Eric R. Cosman, Belmont, MA (US)

(73) Assignee: COSMAN INSTRUMENTS, LLC, Burlington, MA (US)

( * ) Notice: Subject to any disclaimer, the term of this patent is extended or adjusted under 35 U.S.C. 154(b) by 555 days.

(21) Appl. No.: 14/622,783

(22) Filed: Feb. 13, 2015

Related U.S. Application Data

(63) Continuation-in-part of application No. 14/325,285, filed on Jul. 7, 2014, which is a continuation-in-part of application No. 14/325,295, filed on Jul. 7, 2014, which is a continuation-in-part of application No. 14/325,292, filed on Jul. 7, 2014, now Pat. No. 9,717,552, which is a continuation-in-part of application No. 14/325,303, filed on Jul. 7, 2014, which is a continuation-in-part of application No. 14/520,310, filed on Oct. 21, 2014, which is a continuation-in-part of application No. 14/520,305, filed on Oct. 21, 2014, which is a continuation-in-part of application No. 14/530,699, filed on Nov. 1, 2014, which is a continuation-in-part of application No. 14/530,700, filed on Nov. 1, 2014.

(60) Provisional application No. 61/989,479, filed on May 6, 2014.

(51) Int. Cl.
*A61B 18/18* (2006.01)
*A61B 18/14* (2006.01)
*A61B 18/12* (2006.01)
*A61B 18/00* (2006.01)

(52) U.S. Cl.
CPC ...... *A61B 18/1477* (2013.01); *A61B 18/1233* (2013.01); *A61B 18/14* (2013.01); *A61B 2018/00023* (2013.01); *A61B 2018/00797* (2013.01); *A61B 2018/00815* (2013.01); *A61B 2018/00821* (2013.01); *A61B 2018/1425* (2013.01); *A61B 2018/1427* (2013.01)

(58) Field of Classification Search
CPC . A61B 18/1477; A61B 18/1233; A61B 18/14; A61B 2018/00023; A61B 2018/00035; A61B 2018/00797; A61B 2018/00815; A61B 2018/00821; A61B 2018/1425
See application file for complete search history.

(56) References Cited

U.S. PATENT DOCUMENTS 8,882,755 B2 * 11/2014 Leung ................. A61B 18/148
606/20

* cited by examiner

*Primary Examiner* — Robert N Wieland
(74) *Attorney, Agent, or Firm* — Steptoe & Johnson LLP

(57) ABSTRACT

An internally-cooled RF electrode can have a construction that provides for an electrode hub having reduced weight and size.

20 Claims, 10 Drawing Sheets

ELECTROSURGICAL GENERATOR

PRIORITY CLAIM

This application claims priority to U.S. Provisional Application No. 61/989,479, filed May 6, 2014, which is incorporated by reference in its entirety. This application is a continuation-in-part application of U.S. application Ser. Nos. 14/325,295, 14/325,292, 14/325,303, and 14/325,285 filed Jul. 7, 2014, each of which is incorporated by reference in its entirety. This application is also a continuation-in-part application of U.S. application Ser. No. 14/530,699, filed Nov. 1, 2015 and Ser. No. 14/530,700, filed Nov. 1, 2015, which are continuation-in-part application of Ser. No. 14/520,305 and Ser. No. 14/520,310, filed Oct. 21, 2014, each of which is incorporated by reference in its entirety.

TECHNICAL FIELD

This invention relates generally to the advances in medical systems and procedures for prolonging and improving human life. The present invention also relates generally to systems and methods for controlling the output of an internally-cooled electrode by means of a temperature sensor that extends from the electrode active tip. The present invention also relates generally to systems and methods of internally-cooled electrodes having an temperature sensor extending distal to the electrode active tip. The present invention also relates generally to a system and method for applying energy, particularly high-frequency (HF) energy, such as radiofrequency (RF) electrical energy, to a living body. The present invention also relates generally to a system and method for applying energy for the purpose of tissue ablation.

BACKGROUND

The use of radiofrequency (RF) generators and electrodes to be applied to tissue for pain relief or functional modification is well known. For example, the RFG-3C plus RF lesion generator of Radionics, Inc., Burlington, Mass. and its associated electrodes enable electrode placement near target tissue and the heating of the target tissue by RF power dissipation of the RF signal output in the target tissue. For example, the G4 generator of Cosman Medical, Inc., Burlington, Mass. and its associated electrodes (such as the Cosman CSK electrode), cannula (such as the Cosman CC and RFK cannulae), and ground pads (such as the Cosman DGP-PM) enable electrode placement near target tissue and heating of the target tissue by RF power dissipation of the RF signal output in the target tissue. Temperature monitoring of the target tissue by a temperature sensor in the electrode can control the process. Heat lesions with target tissue temperatures of 60 to 95 degrees Celsius are common. Tissue dies and nerves are severed by sustained heating above about 45 degrees Celsius, so this process produces the RF heat lesion. RF generator output is also applied using a pulsed RF method, whereby RF output is applied to tissue intermittently such that tissue is exposed to high electrical fields and average tissue temperature are lower, for example 42 degrees Celsius or less.

RF generators and electrodes are used to treat pain, cancer, and other diseases. Related information is given in the paper by Cosman E R and Cosman B J, "Methods of Making Nervous System Lesions", in Wilkins R H, Rengachary S (eds.); Neurosurgery, New York, McGraw Hill, Vol. 3, 2490-2498; and is hereby incorporated by reference in its entirety. Related information is given in the book chapter by Cosman E R Sr and Cosman E R Jr. entitled "Radiofrequency Lesions.", in Andres M. Lozano, Philip L. Gildenberg, and Ronald R. Tasker, eds., Textbook of Stereotactic and Functional Neurosurgery (2nd Edition), 2009, and is hereby incorporated by reference in its entirety. A research paper by E. R. Cosman, et al., entitled "Theoretical Aspects of Radiofrequency Lesions and the Dorsal Root Entry Zone," by Cosman, E. R., et al., *Neurosurg* 1984; 15:945-950, describes various techniques associated with radio frequency lesions and is hereby incorporated by reference herein in its entirety. Research papers by S. N. Goldberg, et al., entitled "Tissue Ablation with Radio Frequency: Effect of Probe Size, Gauge, Duration, and Temperature on Lesion Volume," *Acad. Radiol.*, Vol. 2, pp. 399-404 (1995), and "Thermal Ablation Therapy for Focal Malignancy," *AJR*, Vol. 174, pp. 323-331 (1999), described techniques and considerations relating to tissue ablation with radio frequency energy and are hereby incorporated by reference herein in its entirety. For a given electrode temperature, size of electrode, and time of heating, you can predict reliably ablation size as described in the papers entitled "Theoretical Aspects of Radiofrequency Lesions and the Dorsal Root Entry Zone," by Cosman, E. R., et al., *Neurosurg* 15:945-950, 1984, and "Bipolar Radiofrequency Lesion Geometry: Implications for Palisade Treatment of Sacroiliac Joint Pain." by E. R. Cosman Jr and C. D. Gonzalez, Pain Practice 2011; 11(1): 3-22 (hereinafter "Cosman and Gonzalez"), which are herein incorporated by reference in their entireties.

The use of high frequency (HF) electrodes for heat ablation treatment in the destruction of tumors is well known. One example is the destruction of cancerous tumors of the kidney using radio frequency (RF) heat ablation. A paper by D. W. Gervais, et al., entitled "Radio Frequency Ablation of Renal Cell Carcinoma: Early Clinical Experience," Radiology, Vol. 217, No. 2, pp. 665-672 (2000), describes using a rigid tissue perforating and penetrating electrode that has a sharpened tip to self-penetrate the skin and tissue of the patient. This paper is hereby incorporated by reference herein in its entirety. A paper by Luigi Solbiati et al. entitled "Hepatic Metastases: Percutaneous Radiofrequency Ablation with Cool-Tip Electrodes," Radiology 1997, vol. 205, no. 2, pp. 367-373 describes various techniques and considerations relating to tissue ablation with RF electrodes which are internally-cooled by circulating fluid, and is incorporated herein by reference. A paper by Rosenthal et al entitled "Percutaneous Radiofrequency Treatment of Osteoid Osteoma," Seminars in Musculoskeletal Radiology, Vol. 1, No. 2, 1997 reports the treatment of a primary benign bone tumor and the management of concomitant pain using a percutaneously placed radiofrequency electrode, and is incorporated herein by reference. United States patents by E. R. Cosman and W. J. Rittman, III, entitled "Cool-Tip Electrode Thermal Surgery System," U.S. Pat. No. 6,506,189 B1, date of patent Jan. 14, 2003; "Cluster Ablation Electrode System," U.S. Pat. No. 6,530,922 B1, date of patent Mar. 11, 2003; and "Cool-Tip Radiofrequency Thermosurgery Electrode System For Tumor Ablation", U.S. Pat. No. 6,575,969 B1, date of patent Jun. 10, 2003 describe systems and methods related to tissue ablation with radiofrequency energy, generators, and internally-cooled RF electrodes, and they are hereby incorporated by reference herein in their entirety. Another example of probes for high-frequency tissue ablation includes microwave (MW) antennae. Another example of probes for tissue ablation are irreversible-electroporation (IRE) probes. Another example of probes for tissue ablation are cryogenic ablation probes.

Examples of cooled RF electrode systems are shown in U.S. Pat. Nos. 5,688,267, 5,735,846, 6,056,745, 6,030,379, and by D. Panescu et al.; U.S. Pat. No. 6,506,189 by W. J. Rittman III and E. R. Cosman; U.S. Pat. No. 7,294,127 by M. Leung et al.; U.S. patent application Ser. No. 11/457,697 by N. Godara and T. Hillier; and U.S. patent application Ser. Nos. 13/153,696 and 14/076,113 by E. R. Cosman Jr. and E. R. Cosman Sr.; each of which is hereby incorporated by reference in its entirety.

Each Cosman CC cannula and RFK cannula, manufactured by Cosman Medical, Inc. in Burlington, Mass., includes a pointed metal shaft that is insulated except for an uninsulated electrode tip. The CC cannula has a straight shaft. The RFK cannula has a curved shaft; one advantage of a curved shaft is that it can facilitate maneuvering of the cannula's tip within tissue. Some cannula include sharp distal points, and some cannula include blunt distal points. Some cannula, for example RFK-C101020B, includes a side opening to the cannula body lumen in the active tip. Each cannula includes a removable stylet rod that can occlude the inner lumen through the cannula's shaft and obdurate the cannula's shaft (which can, for example, facilitate insertion of the cannula into solid tissue), and can be removed to allow for injection of fluids through the cannula shaft and out from the cannula tip, or insertion of instruments, such as an electrode. Each cannula has a hub at its proximal end, the hub sized for manual manipulation of the cannula and having a luer port to accommodate an injection syringe or a thermocouple (TC) electrode, for example the Cosman CSK electrode, Cosman TCD electrode, and Cosman TCN electrode, that can deliver electrical signal output, such as RF voltage or stimulation, to the uninsulated cannula active tip and that can measure the temperature at the cannula active tip. The Cosman CSK and TCD electrodes have a shaft that is stainless steel. The Cosman TCN electrode has a shaft that is Nitinol. One CC or RFK cannula works with one CSK, TCD, or TCN electrode as a two-piece RF electrode system configured for ablation of bodily tissue with temperature control. The Cosman CU electrode is an example of a one-piece RF electrode system wherein the electrode shaft has a tissue-piecing tip, insulation over the proximal shaft to produce an active electrode tip at the shaft distal end, a thermocouple temperature sensor with the active electrode tip, an injection port, a connection to an RF generator, and a lumen within the shaft to provide for fluid injection. The Cosman CR electrode is an example of a one-piece, tissue-piercing, radiofrequency, injection electrode that does not include a temperature sensor. The Cosman CP electrode is an example of a one-piece stimulation electrode system wherein the electrode shaft has a tissue-piecing tip, insulation over the proximal shaft to produce an active electrode tip at the shaft distal end, an injection port, a connection to an nerve-stimulation signal generator (which can be included in an RF generator, in some embodiments), and a lumen within the shaft to provide for fluid injection. Related information is given in Cosman Medical brochure "Four Electrode RF Generator", brochure number 11682 rev A, copyright 2010, Cosman Medical, Inc., and is hereby incorporated by reference herein in its entirety.

Side-outlet RF electrode system include at least one electrode that protrudes from at least one outlet in the side of a cannula shaft. Examples of side-outlet electrode systems are shown in U.S. Pat. No. 4,565,200 by E. R. Cosman, U.S. Pat. No. 5,683,384 by E. J. Gough et al., U.S. Pat. No. 5,672,173 by E. J. Gough and A. A. Stein, U.S. Patent Application Publication Number 20040260282 by E. J. Gough and A. A. Stein, and patent application PCT/US2013/027038 by Stryker Corporation, which are hereby incorporated by reference in their entirety. Examples of side-outlet electrode systems are the SSE Siegfried Side-Outlet Stereotactic Electrode, ZHK Zervas Hypophysectomy Kit, and TCS-1 Side Outlet Stereotactic Electrode Kit systems manufactured by Radionics (Burlington, Mass.) in the 1970s and 1980s. Related information is presented in Cosman E R, Cosman B J. Methods of Making Nervous System Lesions. In: Wilkins R H, Rengachary S S, eds. Neurosurgery. New York: McGraw-Hill; 1984: 2490-2499 which is hereby incorporated by reference in its entirety. Related information is given in the book chapter by Cosman ER Sr and Cosman ER Jr. entitled "Radiofrequency Lesions", in Andres M. Lozano, Philip L. Gildenberg, and Ronald R. Tasker, eds., Textbook of Stereotactic and Functional Neurosurgery (2nd Edition), 2009, which is hereby incorporated by reference in its entirety.

SUMMARY OF THE INVENTION

In one aspect, the present invention relates to an internally-cooled RF electrode having an electrode active tip, configured for insertion into solid bodily tissue, and including temperature sensor that is spaced apart from the electrode active tip, that directly contacts bodily tissue, that has an outer transverse dimension smaller than the outer transverse dimension of the electrode active tip, that does not conduct an RF signal output from an RF generator to the bodily tissue, that is thermally insulated from coolant within the electrode shaft by a layer of thermal insulation and physical separation spanning a substantial distal length of the electrode shaft. In one aspect, the present invention relates to a construction of the said internally-cooled RF electrode that provides for an electrode hub having reduced weight and size.

In one aspect, the present invention relates to an internally-cooled RF electrode having an electrode active tip, configured for insertion into solid bodily tissue, and including an extension temperature sensor that is spaced apart from the electrode active tip at a fixed relative position, that directly contacts bodily tissue, that has an outer transverse dimension smaller than the outer transverse dimension of the electrode active tip, that does not conduct RF signal output to the bodily tissue, that is thermally insulated from coolant within the electrode shaft by a layer of thermal insulation and a gap spanning a substantial distal length of the electrode shaft. In one aspect, the present invention relates to a construction of the said internally-cooled RF electrode that provides for an electrode hub having reduced weight and size.

In one aspect, the invention relates to ablation probes, electrodes, and cannula that can be used in one or more organs in the body, including without limitation organs in the following list: brain, spine, liver, lung, bone, vertebral bone, kidney, abdominal structures, nerves, peripheral nerve, central nervous system, peripheral nervous system, pancreas. The invention relates to probes configured for use for one or more medical applications, including without limitation applications selected from the following list: the treatment of cancerous tumors, treatment of pathological target volumes, treatment of a pain, treatment of movement disorders, treatment of high blood pressure, treatment of cardiac malfunction, or treatment of tissue target volumes in nervous tissue, a nerve located within a bone, bone tissue, cardiac tissue, muscle tissue, or other types of bodily tissues.

Other examples of embodiments of systems and methods of the present invention are given in the rest of this patent. The details of embodiments of the invention are set forth in the accompanying drawings and description below. Other features, objects, and advantages of the invention will be apparent from the description and drawings and from the claims.

BRIEF DESCRIPTION OF THE DRAWINGS

In the drawings that constitute a part of the specification, embodiments exhibited various forms and features hereof are set forth, specifically.

DETAILED DESCRIPTION OF THE INVENTION

Figure 1A:
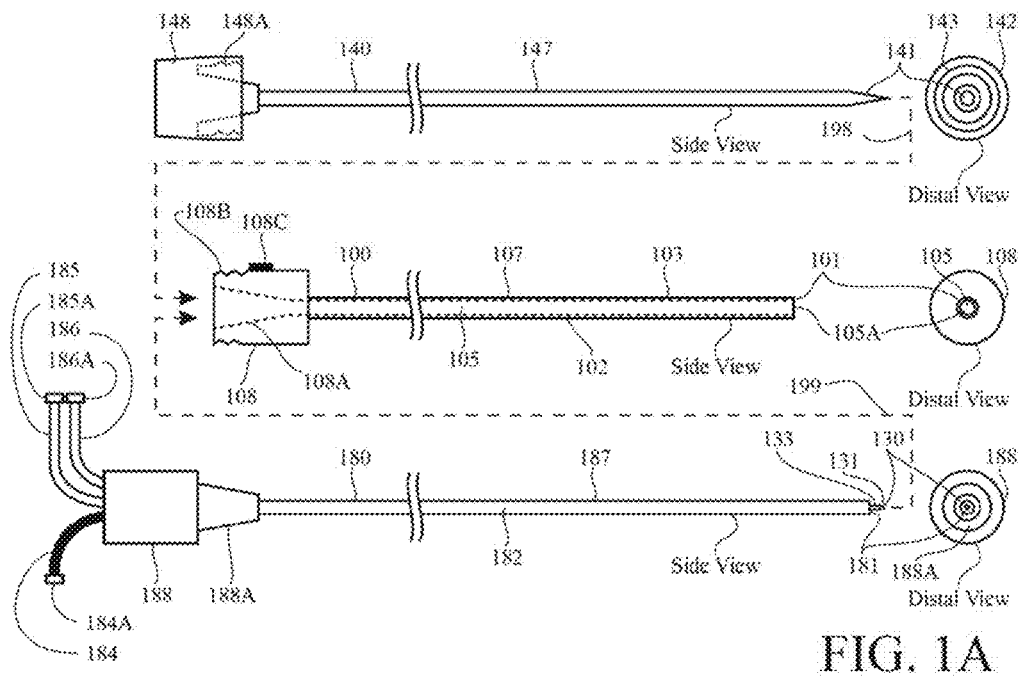
FIG. 1A is a schematic diagram showing a monopolar cooled RF system including a flat-tip internally-cooled RF electrode 180, a straight introducer cannula 100, and a tissue-piercing extension stylet 140 each having a distal tissue-penetrating end and a proximal non-tissue-penetrating end, wherein the extension stylet 140 is configured to extend through a lumen 105 of the cannula 100 and out from opening 105A in the cannula distal end in order to make a path in bodily tissue 190 for subsequent penetration by the electrode 180; the cannula 100 includes fully electrically-insulated shaft 107; the electrode 180 includes electrically-conductive shaft 187 within which coolant fluid circulates and which is configured to be inserted through the lumen 105 of the cannula 100 and out from the opening 105A in the cannula distal end to form electrically-conductive active tip 181A; the electrode 180 includes a temperature-sensor extension shaft 130 that extends a fixed distance distal to the active tip 181A, has a smaller outer diameter than the electrode shaft 187 and active tip 181A, and includes a temperature sensor 131 spaced apart from the active tip 181A; the temperature sensor 131 forms the outer distal surface of the extension shaft 130 to directly contact tissue 190 into which the electrode 180 penetrates; the electrode system is constructed to electrically and thermally insulate the temperature sensor 131 from the active tip 181A and coolant within the electrode 180; the electrode 180 includes a cable 184 that electrically connects an RF potential from an RF generator 170 to the electrode active tip 181A, carries temperature signals from the temperature sensor 131 to a temperature-measurement circuit 172 included in the RF generator 170, and electrically insulates wires carrying electrical signals to the active tip 181A from wires carrying electrical signals from the temperature sensor 131.
Figure 1B:
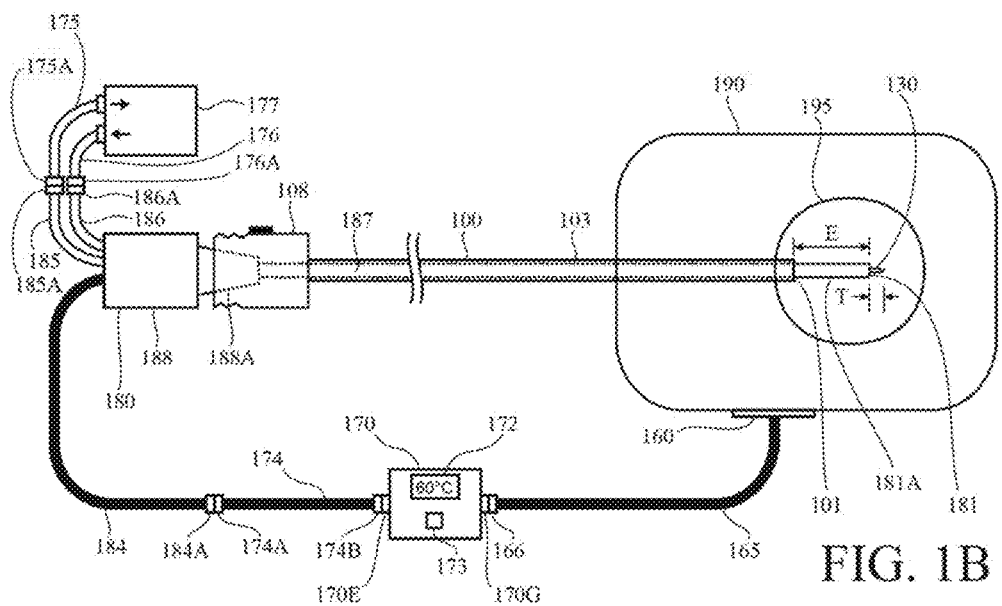
FIG. 1B is a schematic diagram showing the monopolar cooled RF system of FIG. 1A creating a temperature-controlled monopolar heat lesion 195 in bodily tissue 190 by passing RF current between the electrode active tip 181A and ground pad 160 which is positioned on the surface of the bodily tissue 190 and is electrically connected to a reference potential of the RF generator 170; by measuring and controlling the temperature 172 sensed by the electrode coaxial satellite temperature-sensor shaft 130; by circulating coolant fluid from pump 177 through the electrode shaft 187 and its active tip portion 181A; and by keeping the RF potential electrically insulated from the temperature-signal-carrying signals within the electrode, including within the electrode leader cable 184 and extension cable 174 to the RF generator 170.
Figure 1C:
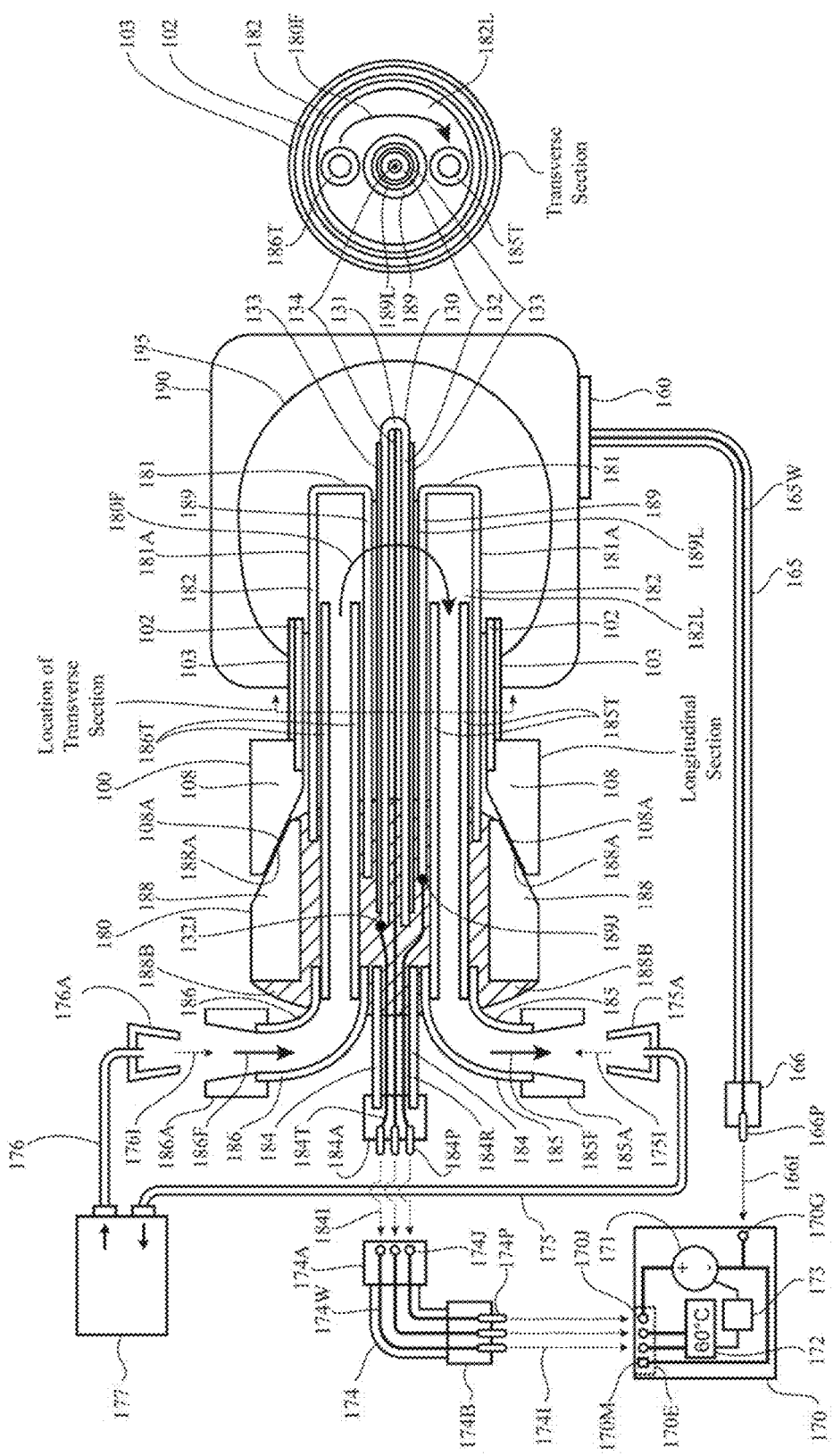
FIG. 1C is a schematic diagram showing one embodiment of the internal construction of the electrode 180, cannula 100, generator 170, coolant pump tubes 175 and 176, ground pad cable 165, and generator extension cable 174 of FIG. 1B, in which the temperature sensor 131 is a thermocouple junction forming the external distal surface of the coaxial temperature-sensor shaft 130, and the temperature sensor 131 is electrically and thermally insulated from the active tip 181A and coolant flow 180F within the electrode 180, generator extension cable 174, and RF generator 170, including by means of plastic coating 133 and gap 189L between the distal lengths of the temperature-sensor shaft 130 and the internal tube 189 of the electrode shaft 187, so that the temperature sensor 131 rapidly senses the temperature of tissue 190 which it contacts, with reduced bias from the temperature of coolant flow 180F within the electrode 180 transmitted through the temperature-sensor shaft 130, and with reduced bias from tissue heating due to RF current flowing through the temperature sensor 131 itself.

Referring now to FIG. 1, in accordance with several aspects of the present invention, FIG. 1 refers collectively to FIG. 1A, FIG. 1B, and FIG. 1C. FIG. 1 presents schematically several embodiments of a electrosurgical ablation probe system including a cannula 100 having a fully-electrically insulated shaft 103 with square cut distal end 101, and internally-cooled RF electrode 180 that extends out of the cannula distal end 101 to define a active tip 181A and that includes an extension temperature sensor shaft 130 which is electrically, thermally, and physically separated from the electrode active tip 181A and the coolant within the electrode shaft 187 over substantially the entire length electrode shaft 887. In one aspect, FIG. 1 relates to an internally-cooled RF electrode 180 that generates an RF ablation zone within bodily tissue and that provides for rapid, accurate measurement of the maximum generated tissue temperature within the ablation zone (or a temperature close to or strongly correlated with said maximum generator tissue temperature), with reduced bias from direct heating of the tissue 190 by RF current flowing through the temperature sensor 131 itself, and within reduced bias from conduction of heat between the temperature sensor 131 and the rest of the internally-cooled electrode 180. In one aspect, FIG. 1 relates to a satellite temperature-sensor structure 130 that is fixedly attached to an internally-cooled RF electrode 180 in order to measure tissue temperature at a predetermined location relative to the electrode active tip 181A, that is mechanically robust to manipulations of the electrode 180 in solid bodily tissue 190, that directly contacts tissue 190 which the electrode 180 penetrates, that does not actively generate RF current capable of substantially heating the tissue 190, and that reduces thermal conduction between the temperature sensor 131 and the rest of the internally-cooled electrode 180 via the temperature sensor's support structure 132. In some aspects, FIG. 1 relates to a method of temperature-controlled cooled RF tissue ablation whereby tissue 190 at a predetermined location relative to the active tip 181A is measured and controlled by means of an electrically-passive, high-speed temperature sensor 131 that is thermally insulated from the internally-cooled portions 182L of the electrode 180. In some aspects, FIG. 1 relates to a method for using a thermocouple temperature sensor 131 to control tissue temperature at a fixed location relative to the active tip 181A of an internally-cooled RF electrode 180 with reduced bias from tissue heating due to RF current generated by the temperature sensor 131 and from heat sinking through the support structure 132 of the thermocouple 131 to the coolant within the electrode.

FIG. 1 shows a medical probe system including a cooled RF electrode 180, a cannula 100, and an extension stylet 140, each including a distal tissue-penetrating end, and a proximal non-tissue-penetrating end. The electrode includes integral generator connection cable 184 which includes plug 184A and is configured to carry RF current from an RF generator 170 to the electrode shaft 187 and to carry a temperature signal from the electrode extension temperature sensor 131 to the RF generator 170; hub 188 at the electrode proximal, non-tissue-penetrating end, the hub having a male luer taper 188A; a substantially straight shaft 187 comprising a conductive metal tube 182 configured to conduct the RF current from the RF generator 170 to the cannula active tip region 181A which includes a flat, closed distal end 181 and which is the distal portion of the tube 182 that protrudes distal to the cannula distal end 101 when the electrode shaft 187 is inserted into the cannula lumen 105 through the cannula hub port 108A; a coaxial satellite temperature sensor shaft 130 protruding distal from the distal tip 181 of the active tip 181A and including a temperature sensor 131 at its distal end, and electrically-insulated proximal shaft portion 133; coolant inflow tube 186 which includes connector 186A and through which coolant (such as water or saline, which can be sterile or non-sterile, which can be cooled or at room temperature, in various embodiments, to suit clinical needs) can be pump into shaft 187; and coolant outflow tube 185 which includes connector 185A and through which coolant can exit shaft 187. The cannula 100 is configured to penetrate tissue in concert with the stylet 140, to provide a channel for insertion of the electrode 180 into tissue, and to define the active tip region 181A of the electrode for delivering of RF current to bodily tissue 190 from the electrode 180. The cannula 100 includes hub 108 at the cannula proximal, non-tissue-penetrating end, the hub including proximal female luer port 108A connected to the lumen 105 of the straight tubular shaft 107 and sized to engage with the electrode male-luer hub taper 188A; hub threads 108B on the exterior surface of the hub 108 that are configured to engage with the stylet cap threads 148A and thereby rigidly and releasably attached stylet 140 and cannula 100; straight shaft 107 composed of conductive metal hypodermic tubing 102 whose proximal end is fully covered by electrical insulation 103, the shaft length being configured so that the electrode distal end 181 exits the opening 105A when the electrode shaft 187 is fully inserted into the cannula lumen 105 through the cannula hub port 108A such that the electrode hub luer 188A engages with the cannula hub luer 108A; and lumen 105 through the cannula shaft 107 sized to admit the electrode shaft 187; square-cut distal end face 101, the face surrounding distal opening 105A to the cannula lumen 105. The stylet 140 is configured to be inserted into the cannula 100 to stiffen the cannula shaft, to occlude the distal open 105A of the cannula shaft 107 during tissue penetration, and to pierce solid tissue 190 distal to the cannula 100 thereby creating a path through which the electrode 180 can be inserted without damaging the extension temperature sensor assembly 130. The stylet 140 includes cap 148 at the stylet proximal, non-tissue-penetrating end, the cap 148 including internal thread 148A configured to engage with the treads 108A of cannula hub 108 and thereby removably connect the stylet 140 and cannula 100 to form a single tissue-piercing probe; and elongated shaft 147 configured to be inserted into the cannula lumen 105 and including sharpened conical tip 141 at the stylet distal tissue-penetrating end, the tip 141 being configured to piece and penetrate solid bodily tissue 190. The electrode shaft 187 is not shaped to define a bend. In some embodiments, the electrode shaft tube 182 can be constructed from a stainless steel tube that is substantially straight. In some embodiments, the metal hypodermic tubing 102 can be stainless steel hypodermic tubing. The electrical insulation 103 and 133 can each be a plastic coating or plastic tubing, of the same or different types, of the same or different wall thicknessness. In some embodiments, the size of the cannula tubing 102 can be a value selected from a value or range in the list: 20, 19, 18, 17, 16, 15, 14, 13 gauge, larger than 13 gauge, less than 20 gauge. The wall thickness of the cannula tubing 102 and the wall thickness of the electrode shaft tubing 182 can be selected from regular wall, thin wall, heavy wall, and special wall-thicknesses. In some embodiments, the outer diameter of the electrode shaft 187 can be a value selected from a value or range in the list: 22 to 15 gauge, greater than 15 gauge, less than 22 gauge, a diameter less than the inner diameter of the cannula. In some embodiments, the length of the shaft 107 of the cannula 100 can be a value selected from a value or range in the list: 5, 6, 10, 12, 15, 20, 25, 30 cm, less than 5 cm, greater than 30 cm, 5-30 cm. In some embodiments, the length E of the active tip 181A of the electrode 180 can have a value selected from a value or range in the list: 0, 1, 2, 3, 4, 5, 10, 15, 20, 25, 30, 40, 50, 60 mm, 0-60 mm, greater than 60 mm. In some embodiments, the length T of the extension temperature sensor shaft 130 can have a value selected from a value or range in the list: 0.010, 0.015, 0.020, 0.025, 0.030, 0.035, 0.040, 0.080, 0.120, 0.160 inches, 0.010-0.160 inches, less than 0.010 inches, greater than 0.160 inches, 0.400 inches, greater than 0.400 inches, a length configured to position the temperature sensor 131 at or near the most likely location of maximum tissue temperature during generation of an cooled RF heat lesion by internally-cooled RF electrode 180, a length configured position temperature sensor 131 to measure a tissue temperature which produces stable cooled RF lesions in a variety of tissue conditions when controlled by the generator, a length configured to measure the temperature of a structure that a physician desired not ablate during an ablation process. In some embodiments, the outer diameter of the extension temperature shaft 132 can be a value selected from the following list, or a value from a range in the said list: 30, 29, 28, 27, 26 gauge, a diameter in the range 30-26 gauge, larger than 26 gauge, smaller than 30 gauge, smaller than the outer diameter of electrode shaft tube 182, a small value selected to minimize thermal conduction along shaft 132, a small value selected to increase the spatial locality and speed of temperature measurement by thermocouple 131. In some embodiments, the electrode male luer 188A and the cannula female luer 108A can take another interlocking or complementary form that allows for seating of the electrode hub 188 against the cannula hub 108. In some embodiments, extension temperature shaft 130 includes multiple temperature sensors each of which produces a temperature signal measured by generator 170 for display to the user and control of the RF output level delivered by the generator 170.

Referring now to FIG. 1A, the electrode 180, the cannula 100, and the stylet 140 are shown separately, and each is shown in both a view from the side ("Side View") and from the distal end (ie looking toward the proximal end) ("Distal View"). The inner wall of the cannula 100, including the inner wall of the hub port 108A and the inner wall of shaft tube 102, is shown in the Side View as a dashed line through the solid side walls of the hub 108 and shaft tubes 102 and 103.

Referring now to FIG. 1B, the cannula 100 and electrode 180 are shown assembled and producing a monopolar cooled RF heat lesion 195 in bodily tissue 190 by application of RF current to the tissue from the electrode active tip 181A, which is the portion of the electrode shaft 187 extending out from the distal opening 105A of the cannula shaft 107, while pump 177 circulates coolant fluid through electrode shaft 187, including through the active tip region 181A. The distal hub taper 188A and the shaft 187 of the electrode 180 are shown as dotted lines in the Side View through the solid walls of the cannula 100. This configuration was produced by the process of inserting the cannula 100 into the bodily tissue 190 with the stylet 140 fully inserted into the cannula lumen 105 via the cannula hub port 108A and with the stylet hub cap threads 148A screwed on the cannula hub threads 108A; unscrewing and withdrawing the stylet 140 from the cannula lumen 105 through the cannula hub port 108A; inserting the electrode 180 into the cannula lumen 105 by way of the cannula hub port 108A; connecting pump 177 to the electrode inflow tube 186 via extension tube 176 having connector 176A; connecting pump 177 to the electrode outflow tube 185 via extension tube 175 having connector 175A; running pump 177 to circulate fluid coolant through the electrode shaft 187 and active tip 181A; connecting RF generator 170 to the electrode 180 via generator extension cable 174; connecting RF generator 170 to a ground pad 160 placed on the surface of the bodily tissue 190 via ground pad cable 165; delivering RF current from the RF generator 170 between the electrode 180 and ground pad 160, which are connected to opposite poles ("+" and "−") of the RF power supply 171 within generator 170; and controlling the RF current output of the RF generator using the temperature 172 measured by the electrode temperature sensor 131 and displayed by the RF generator 170, in accordance with user controls 173. In this example, the measured temperature 172 is 60° C., but can vary depending on the output of the RF generator, generator settings, tissue properties, coolant temperature, coolant flow rate, and other factors. The said process is one example of a process for controlling formation of a heat lesion 195 by measuring tissue temperature distal to the electrode active tip 181A. The said process is one example of a process for creating an enlarged heat lesion 195 around a probe active tip 181A using tissue-temperature monitoring. In some embodiments, the outflow of coolant from tube 185 is directed not back to the pump apparatus 177, but to a discard reservoir. In some embodiments, pump 177 recirculates coolant from the electrode outflow 185 back to the electrode inflow 186. In some embodiments, pump 177 does not recirculate coolant from the electrode outflow 185 back to the electrode inflow 186.

The cannula 100 is inserted into bodily tissue 190, the electrode 180 is fully inserted into the cannula 100 such that the electrode hub taper 188A engages with the cannula hub port 108A, a portion of the electrode shaft 181A extends from the distal opening 105A of the cannula. Ground pad 160 is applied to the surface of the bodily tissue 190 connected to the reference jack 170G of an RF generator 170 via connection 166. Electrode 180 is connected to the multi jack electrode RF port 170E of the RF generator 160 via extension cable 174 and electrode leader cable 184. A temperature signal form the electrode temperature sensor 131 is conducted through cables 184 and 184 to RF generator 170 for control and/or display. RF current flows from the RF generator 170 via the connection 174 and 184 to the conductive electrode shaft tube 182 and its active tip portion 181A extending from the cannula distal opening 105A into the tissue 190, and the RF current returns to the RF generator 170 via the ground pad 160. By ohmic heating, the RF current within the bodily tissue causes the tissue temperature to increase around the conductive active tip 181A of the electrode shaft 187 extending distal to the cannula 100.

The electrical insulations 103 and 133 are each a tubular structure that is electrically insulative at electrical signal frequencies intended to be delivered deliver to bodily tissue via the electrode 180. In some embodiments, said signal frequencies can include radiofrequency signal frequencies, microwave (MW) signal frequencies, the signal frequencies associated with nerve stimulation signals, the signal frequencies associated with muscle stimulation signals, high frequency signal frequencies, low frequency signal frequencies and other signal frequencies applied via probes and other electrodes to bodily tissue. Each insulation 103 and 133 can have a high dielectric constant. The dielectric breakdown (also known as the dielectric strength) of each of the insulations 103 and 133 can be greater than 500 V/m. Each of the electrical insulations 103 and 133 can have a wall thickness that is a value selected from a value or range of value in the list: a value in the range 0.00025 to 0.005 inches, 0.001 inches, 0.002 inches, 0.001-0.002 inches, a value less than 0.00025 inches, a value greater than 0.005 inches. Each of the electrical insulations 103 and 133 can have wall thickness in the range 0.001 to 0.002 inches. Each of the electrical insulations 103 and 133 can have wall thickness configured to suit clinical needs, mechanical constraints, thermal requirements and/or electrical requirements. Each of the electrical insulations 103 and 133 can be composed of a material known in the art of medical device design, such as PTFE, FEP, PET, polyolefin, polyurethane, polyimide, nylon, and other materials for medical tubing. Each of the electrical insulations 103 and 133 can be heat-shrinkable tubing, such as PTFE, FEP, PET, polyolefin, and other materials known in the art of medical device coating, such as needle, wire, guidewire, and coil coating. Each of the electrical insulations 103 and 133 can be tapered and/or adhered to its respective shaft 102 or 132 at the distal end of the insulation. In some embodiments, each of the electrical insulations 103 and 133 can be an electrically-insulative coating, such as a coating that can be painted or sprayed onto its respective tube 102 or 132, such as an elastomeric coating, powered paint, fluid paint, or another kind of paint. Temperature sensor shaft electrical insulation 133 can be configured to have superior thermally-insulative properties to limit heat transfer to internally-cooled structures of the rest of electrode 180 and thereby reduce bias in the tissue temperature measured by temperature sensor 131.

In some embodiments, the cannula conductive shaft tube 102 can include a distal portion that this not covered by electrical insulation 103, so that said distal portion is a cannula active tip that is brought to the same electrical potential as the electrode conductive shaft 182 and active tip 181A when the electrode is inserted into the cannula lumen by means of physical contact between the outer wall of the electrode shaft tube 182 and the inner wall of the cannula shaft tube 102, and thus so that the cannula active tip and the electrode active tip 181A form a combined monopolar active tip through which electrical current can flow through tissue 190 in which the combined active tip contacts. In some of these embodiments, the distal end 101 of the cannula 100 can be alternatively configured to include sharpened bevel configured to pierce and penetrate solid bodily tissue 190, such as a flat angled bevel, a tricut bevel, a sharp tapered distal edge, and other bevel point with a lumen opening known to those skilled in the art. In some embodiments, the distal end of the cannula 101 and/or the distal end of the stylet 141 can be configured to provide for penetration into bone, such as vertebral bone or any bone in the body, for access to nerve within bone, osteoid osteoma, bone tumors, or another intra-bone structures. In some embodiments, the stylet shaft 147 can have a length sized to extend beyond the distal end 101 of the cannula by either greater, or less, or equal to the extent by which the electrode 180 extends beyond the cannula distal end 101 when the electrode 180 is fully inserted into the cannula 100. In some embodiments, the cannula 100 and electrode 180 can be configured to be placed in a specific part of the body such as the spine, a blood vessel, the epidural space, the spinal cord, a visceral organ, the liver, the kidney, the pancreas, the lung, the brain, a gland, the tyroid, the adrenal gland, a bone, a vertebral bone.

Referring now FIG. 1C, the system and operational cooled-RF lesioning configuration of FIG. 1B are presented in a different schematic diagram in which each of the electrode 180, cannula 100, generator 170, cable 174, cable 184, tubing connection 175A, and tubing connection 176A are shown in a cross-sectional view; the cable and tubing connections are exploded for clarity; and in which the location of the transverse cross section ("Transverse Section") of the assembled electrode 180 and cannula 100 is indicated in the longitudinal cross-section ("Longitudinal Section") by the line labeled "Location of the Transverse Section". The releasable conductive connection of ground pad pin 166P and reference jack 170G, which is shown in an exploded view, is shown by arrow 1661. The releasable electrical connection of pins 174P of cable 174 to four jack electrode port 170E of generator 170, which is shown in an exploded view, is indicated by arrow 1741. The releasable electrical connection of pins 184P of cable 184 to jacks 174J of cable 174, which is shown in an exploded view, is indicated by arrow 1841. The fluid-tight releasable connection of tapered connector 175A of tube 175 to complementary port 185A of tube 185, which is shown in an exploded view, is indicated by arrow 1751. The fluid-tight releasable connection of tapered connector 176A of tube 176 to complementary port 186A of tube 186, which is shown in an exploded view, is indicated by arrow 1761. The opposite sides of each tubular structure of electrode 180 (for example tube 182) appear separately on opposite sides of the tube axis.

Generator 170 includes thermocouple temperature measurement circuit and display 172, user controls and automated controller 173, RF power supply 171. Ground pad jack 170G is electrically connected to the "−" pole of RF supply 171 for monopolar RF operation. Four-contact electrode jack 170E includes four jacks, which include RF jack 170J and reference jack 170M, is configured to connect to an electrode (eg 180, 280, 380A, 380B, 380C, 380D, 480, 580, 680, 780, 880) either directly or via an extension cable (eg 174). Reference jack 170M is electrically connected to the "−" pole of RF supply 171 for bipolar RF operation (as shown in FIG. 2 for example). The opposite pole "+" of the RF supply 171 is electrically connected to jack 170J for connection to an RF probe active tip.

Extension cable 174 includes generator pins 174P, electrode jacks 174J, generator connector 174B, electrode connector 174A, three insulated wires 174W each electrically connecting a jack 174J at one end of the cable to a pin 174B at the other end of the cable such that the jacks 174J are electrically isolated from each other, and the pins 174P are electrically isolated from each other.

Ground pad cable 165 conducts the "−" reference potential from RF supply 171 to the ground pad via wire 165W.

The cannula hub 108 is attached to stainless steel hypodermic tube 102 of the cannula shaft 107, which is fully covered by electrically-insulative plastic tube 103. The cannula lumen is bounded by hub port 108A and the inner wall of tube 102.

The stainless-steel electrode shaft 187 includes an outer tube 182, flat annular distal face 181, and stainless-steel inner tube 189, which are welded together at the distal end of the shaft 187 to seal closed the distal end of lumen 182L between tubes 182 and 189 and contain the coolant fluid 180F flowing therein. One advantage of outer shaft 182, inner shaft 189, and closed distal end 181 being composed of rigid metal and fused together by a rigid metallic joint (eg by welding or soldering) is that they can contain high coolant pressure 180F and high flow rate, thereby enabling generation of larger ablation zone with less risk of unintended leakage of coolant fluid into bodily tissue. In some embodiments, the inner tube 189 and outer tube 182 can be fused at the distal end by one or more of the list: solder, welding, conductive glue, mechanical crushing, melting. The proximal end of lumen 182 is sealed by glue 188B within hub 188. Coolant fluid enters the lumen 182L by flowing through tube 186 as indicated by arrow 186F, and then through shaft inflow tube 186T whose distal end opening is near the distal end of the lumen 182L, for example within 2-4 mm of the distal end, or another distance configured to provide for unrestricted coolant flow within the active tip region 181A, with regular turnover of coolant fluid within the active tip region 181A. Coolant fluid exiting inflow tube 186T fills the lumen 182L, exits the shaft outflow tube 185T as indicated by arrow 180F, and flows out of the electrode through tube 185T and tube 185. Shaft tubes 185T and 186T can be metallic or plastic tubes, being made of stainless steel, polyimide, and/or other materials known to those skilled in the art of medical device manufacturing. The tubes 185T and 186T can be thin walls to maximize the transverse cross-sectional area of the shaft through which coolant fluid can flow. Use of plastic tube 585T and/or plastic tube 586T has the advantage of reducing metal content to reduce artifacts in MRI and CT imagine of the electrode 180. Use of a very thin wall plastic tube, eg 0.0005-0.002 inches wall thickness has the special advantage of maximizing fluid flow and being electrically insulative to avoid inadvertently shorting together wires and other conductive structures within the electrode 180. Transverse Section shows that tubes 185T and 186T taking up a small portion of the transverse cross-sectional area of the electrode shaft 187 in the schematic diagram FIG. 1C. In some embodiments, the lumens of tubes 185T and 186T can be limited to limit the flow rate of coolant 180F and thereby limit RF lesion size. In some embodiments, the lumens of tubes 185T and 186T can consume a large or maximal portion of the transverse cross-sectional area of the electrode shaft 187 to increase the flow rate of coolant flow 180F and thereby increase RF lesion size. In some embodiments, the lumens of tubes 185T and 186T have equal cross-sectional area to increase the flow rate of coolant flow 180F and thereby increase RF lesion size. The wall thickness of outer tube 182 and distal end face 181 can be very thin to maximize heat conduction from the tissue 190 into the coolant 180F. One advantage of a flat distal end 181 having a constant thin wall thickness (for example in the range 0.001 to 0.005 inches) is that heat conduction is increased to the coolant 180F from tissue immediately distal of the electrode active tip 181A, where tissue temperatures are hottest and thus where boiling can lead to gas formation that limits lesion size.

One advantage of a flat distal end 181 is that the electric field strength at the center of the distal end 181 is reduced relative to a distal end geometry having greater curvature, thereby reducing direct tissue heating immediately distal of the electrode active tip 181A, where tissue temperatures are hottest and thus where boiling can lead to gas formation that limits lesion size.

RF output "+" from supply 171 is conducted through a wire of extension cable 174, through a wire of leader cable 184, through junction 189J (which can be a solder joint, in one example), through conductive stainless steel inner-shaft tube 189, through the outer shaft tube 182 and distal end 181 to bodily tissue 190. In some embodiments, junction 189J can attach a cable wire carrying the RF output to another structure electrically-conductively connected to the electrode outer shaft tube 182 and thus the electrode active tip 181A, such as the tube 182 itself, tube 185T if 185T composed of a conductive metal, or tube 186T if 186T is composed of a conductive metal. In some embodiments in which the RF wire is connected to outer shaft tube 182, the inner shaft tube 189 can be non-electrically-conductive and joined to outer tube 182 by a non-conductive means, such as glue.

Extension temperature sensor assembly 130 includes insulated constantan wire 134, stainless steel tube 132, electrical insulation tube 133, and weld between stainless steel tube 132 and constantan wire 134 forming thermocouple 131 and closing the distal end of tube 132. A first input pole of temperature measurement circuit and display 172 is connected thermocouple 131 by a first wire of cable 174, a first wire of cable 184, and constantan wire 134. A first input pole of temperature measurement circuit and display 172 is connected to thermocouple 131 by a second wire of cable 174, a second wire of cable 184, conductive junction 132J (which in some embodiments can be a solder joint, or solder joints and a jumper cable) and stainless steel hypotube 132. Hypodermic tube 132 is configured to provide structural support to temperature sensor 131 through manipulations of electrode 180 within solid bodily tissue 190. Hypotube 132 is configured to be small (for example 26-30 gauge, or preferably 28 gauge) to minimally conduct heat from tissue 190 to coolant 180F within the electrode. Weld 131 is configured to be small and metallic in order to rapidly sense the temperature of tissue 190 in which it is in direct contact. Advantageously, thermocouple weld 131 directly contacts bodily tissue 190 in order to rapidly and accurately sense the temperature of tissue in which it is in contact, without any intervening material (such as an external metallic shell enclosing the temperature sensor 131, glue potting the temperature sensor 131, or electrical insulation covering the temperature sensor) that would slow down and/or spatially blur the thermal response, for example, due to the volume, density, specific heat, thermal conductivity, and other physical characteristics of an intervening material that influence conduction of heat to the temperature sensor 131 from tissue 190. Hub glue 188B rigidly anchors extension temperature sensor assembly 130 to the rest of the electrode and fixes the position of temperature sensor 131 relative to the active tip 181A. The temperature-sensor shaft 130 is not connected to the inner wall tube (or the rest of the electrode) over the distal end of the temperature-sensor lumen 189L. Gap 189L extends over the entire distal length between the inner wall of tube 189 and the outer wall of the temperature-sensor shaft 130. It is understood that the outer surface of the temperature-sensor shaft 130 can touch the inner wall of tube 189 at some points along its length, for example, due to minor departures from perfect straightness in either the tube 189, or the temperature-sensor shaft 130, or both. The inner tube wall 189 is one example of a fluid-tight barrier between the coolant 180F and the temperature sensor shaft 130. Thermally-insulative plastic sheath 133 cover the entire portion of temperature-sensor shaft 130 that is within the electrode shaft tube 182 and 189, and covers all of the temperature-sensor shaft 130 that extends into bodily tissue 190 distal to the electrode active tip 181A except for the temperature sensor 131 at the distal end of shaft 430. As such, both the gap 189L and thermally-insulative sheath 133 reduce thermal conduction between coolant flow 180F within the electrode fluid lumen 182L and thereby advantageously reduce bias in the tissue temperature sensed at thermocouple 131 due to thermal conduction along the metallic thermocouple shaft 132. In addition, the thermally insulative sheath extending distal to the electrode active tip 181A limits heat conduction into and thus along the portion of the metallic shaft 132 that contacts tissue immediately distal to the electrode active tip 181A; this had the advantageous effect of limiting the excessive blurring of tissue temperatures just distal to the electrode active tip 181A, which are cooled by the cooled active tip 181A, and thus providing a more spatially precise temperature measurement by temperature sensor 131. This is an important advantage of temperature sensor extension shaft 130, whose proximal portion is thermally insulated and whose distal metallic temperature sensor directly contact tissue 190. In contrast, due to the generally high thermal conductivity of metals, a metallic surface covering the entire length of a temperature-sensor shaft protruding from an internally-cooled electrode active tip can blur temperatures within the region immediately distal to the cooled active tip (effectively averaging the temperatures over the region), where thermal gradients are very high (meaning that temperatures change by a large amount over a short distance), thus confounding precise measurement of temperature at a desired location distal to the active tip. Thus, one advantage of temperature-sensor shaft 130 is the ability to sense temperature rapidly and accurately at a precise location spaced from the electrode active tip 181A, by means of direct contact between its small, metallic temperature sensor 131 and bodily tissue, by means of thermal insulation covering the portion of its shaft that is proximal to the temperature sensor 131 and distal to the active tip 181A, by means of thermal insulation and a physical gap between the temperature sensor shaft and the coolant lumen 482L within the electrode shaft 187, and by means of electrical insulation between the temperature sensor 131 and the electrode active tip 181A within the electrode 180, cables 184 and 174, and generator 170. One advantage of extension thermocouple structure 130, which supports only a single thermocouple 131, is that the shaft diameter can be minimized to reduce thermal conduction along the shaft that could bias the temperature sensed by thermocouple 131. In some embodiments, more than one temperature sensors can be positioned along the portion of shaft 132 that extends out from the electrode distal end 181 in order to measure temperatures at multiple locations distal to the active tip 181A; in some embodiments, each of said more than one temperature sensors can directly contact bodily tissue by welding an insulated constantan wire to a location along shaft 132 to form a thermocouple. In some embodiments, additional temperatures can be included along the length of shaft 132 within the electrode inner shaft tube 189. In some embodiments, the thermocouple 131 can be formed by a different means of joining the constantan wire 134 and stainless steel tube 132, such as soldering. In some embodiments, thermocouple 131 can be formed by joining two thermocouple wires that are threaded through the lumen of extension shaft tube 132, and the thermocouple can be fixed to the distal end of the shaft tube 132.

Hub glue 188B rigidly anchors together the electrode hub 188, shaft 187, shaft tubes 185T and 186T, and satellite temperature sensor shaft 130. Hub glue 188B is electrically-insulative to prevent shorted circuiting of thermocouple potential to the RF potential. Hub glue 188B creates a fluid-tight seal that prevent flow of fluid from the lumen 182L into gap 189L, into the lumen of thermocouple shaft 132, or out from the hub 188 except through tubes 185 and 186. In some embodiments, glue 188B can be replaced by one or more of the following to produce a similar functional effect: gasket, spacer, clamp, plug, epoxy, an over-molded part. One important advantage of hub glue 188B and the construction of hub 188 is that it provides for a simple and compact assembly of the electrode 180, and electrical isolation of conductive elements therein, thereby allowing the dimension and weight of the hub 188 and the whole electrode 180 to be reduced. Reduction of the dimension and weight of the hub 188 and the whole electrode 180 has advantages, including facilitating use of the electrode 180 in the bore of an MRI scanner, facilitating use of the electrode 180 in the small bore of an high-field-strength MRI scanner, reducing the likelihood of the electrode being displaced by the hub weight for more shallow insertions of the electrode shaft 187 into bodily tissue 190, allowing for close spacing of multiple electrode 180 for the purpose of clustered RF lesioning or inter-electrode bipolar RF lesioning.

Electrical insulation over cable wires 174W, 184R, 184T, and 134; thermocouple shaft insulation 133; electrically-insulative hub glue 188B; and electrical insulation within the generator 170, as well as the relative spacing of these elements are configured to limit the flow of RF current (by conduction, induction, and/or capacitive coupling) from generator 170 directly from the thermocouple temperature sensor 131 and into tissue 190, thereby advantageously limiting direct ohmic heating of tissue nearby sensor 131 so that sensor 131 provides an accurate measure of the heating effect of the internally-cooled active tip 181A on tissue 190.

In some embodiments, electrical insulation 133 can be applied to the inner wall of electrode inner shaft tube 189, rather than to the temperature sensor shaft 132. In some embodiments, the inner shaft tube 189 is made from an electrically insulative material, the RF output wire 184R is wired directly to electrode conductive outer shaft tube 182, and the thermocouple shaft insulation can be omitted.

In some embodiments shaft 187 can be composed of one or more conductive substances to suit clinical and performance needs, such as titanium, platinum silver, gold, solder, and other metals. In some embodiments, conductive structures of the electrode 180, cannula 100, cable 174, ground pad 160, and other components can be composed of "MRI-safe" alloys, such as titanium, to provide for use within an MRI scanner.

As in some embodiments presented in U.S. application Ser. Nos. 14/325,295, 14/325,292, 14/325,303, and 14/325,285, in some embodiments of the present invention, electrode 180 includes an extension tip 130 that houses a temperature sensor 131 configured to monitor tissue temperature distal to the active tip 181A of the electrode 180, close to or at the location of maximum tissue temperature. The generator settings 173 include a set temperature value of 95° C. The combination of the extension tip temperature sensor 131 and the set temperature 173 are configured to hold the maximum tissue temperature just below the boiling point in order to maximize heat lesion size and to prevent tissue boiling. The generator control system is adapted to measure the extended temperature from sensor 131, and to display the extended temperature 172 on the computer graphic display 172 together with other signal output parameters in the list of power, current, voltage, and impedance. The control system 173 is can be adapted to use the extended temperature 131 as a feedback parameter in the ablation process. In one example, the extended temperature can be a check that the boiling bubble zone, or potential boiling bubble zone, is in the desired range of temperature and time duration. By displaying the extended temperature 131 along with the other output parameters and, the clinician can have visual check and confirmation of the ablation process. Electrode 180 is connected to generator electrode jack 170J via cable 174 and 184 that carries HF output to the electrode 180. Coolant, such as chilled saline or water, is pumped through tube 176 and 186 into the electrode 180, flows through the electrode shaft 187 to cool the active tip 181A, and out from the electrode through tube 175 and 185, and into collection container within pump 177. Electrode 180 includes a combined hub 108 and 188 at the electrode proximal end, an elongated shaft including an insulated portion 103 at the shaft proximal end and a conductive active tip 181A at the shaft distal end, an extension tip 130 extending distal to the distal end of the active tip 181A, wherein the extension tip 130 includes a temperature sensor 131 at a distance T from distal end of the active tip 181A, wherein the distance between the extension tip temperature sensor 131 and the distal end of active tip 181A be a value in the range 0.1 mm to 10 mm (or value adapted to locate the temperature sensor at the most likely location of maximum tissue temperature), wherein the insulated portion 103 prevents outflow of the generator's HF output signal, and wherein active tip 181A allows outflow of the generator's HF output signal 171 to the bodily tissue of an organ of body 190 and thereby generates heat lesion 195. In some embodiments, the temperature sensor 131 can be at the distal end of the extension tip 131. In some embodiments, electrode 180 is introduced into bodily tissue by means of an introducer cannula 100 that can be tissue-piercing or that can be configured to be tissue-piercing by means of a sharp-point stylet 140. In some embodiments, the introducer cannula 100 can have sharp bevel at its distal, and a removable stylet with match-ground distal bevel, to reduce insertion forces when the cannula 100 is inserted into patient tissue 190. The distal extension tip 130 can be electrically insulated (for example by electrical insulation 133 and other electrical insulation within electrode 180 and cable 174) so that the extension tip 130 does not produce HF heating of the tissue by itself, and thus less influences the temperature of the tissue at a distance T from the end of the active tip. The distance T can be predetermined so that sensor is located in the hottest part of the tissue during ablation. Alternatively, the distance T can be adjustable by the user if the extension tip 130 is configured to slide relative to the active tip 181A. In some embodiments, such as electrode 680 shown in FIG. 6, the extension tip 630 can be slidably mounted to the active tip 681A, perhaps via other elements of the electrode 680, such as a clamp 637 and 638 in the electrode hub 688, so that the user can measure temperature at multiple locations distal to the tip 681A by sliding the extension tip 630 relative to the active tip 181A. In some embodiments, the extension tip 130 can be fixedly mounted to the active tip 181A, such as via hub glue 188B in electrodes 180. In some embodiments, the distal extension tip 130 can comprise a stainless steel tube 132, a temperature sensor 131 at the distal point of the tube 132 (for example, formed by welding a constantan wire 134 within the stainless steel tube 132 to the distal end of the stainless steel tube 132), electrical insulation 133 (which can comprise a plastic coating or sheath along the tube 132, and glue 188B covering wire connections 132J, 189J at the tube proximal end) covering all but the distal point 131 of the tube 132; wherein the tube proximal end is positioned within an inner lumen 189L of the electrode shaft 187 and tip 181A (for example, the lumen 189L can be formed by a pipe 189 within the shaft 187 and tip 181A that is welded to the distal end of the pipe 182 that forms the outer surface of the tip 181A, between both of which pipes 182 and 189, the coolant fluid flows 180F and is contained), the tube 132 position is fixed relative to the active tip 181A by a thermally-insulative element at a proximal location within the electrode 180 (for example, by glue 188B within the electrode hub 188), and the extension tip 130 is thereby thermally, electrically, and physically separated from both the active tip 181A and the coolant flow 180F within the electrode shaft 187 and tip 181A, both by a physical gap 189L (ie the space between inner surface of the lumen 189L and the outer surface of the tube electrical insulation 133) and the electrical insulation 133 covering the tube 132; and wherein the wires 184T and 134 connecting to the extension tip temperature sensor 131 to the generator 170 are electrically isolated from the HF output wires 184R in the electrode 180, cables 184 and 174, and generator 170; so that the extension tip 130 does itself produce HF heating of the tissue 190, and the extension tip 130 measures temperature of the tissue at a distance T from the end 181 of the active tip 181A with a fast thermal response due to the metallic temperature sensor 131 that is integral with the outer surface of the distal end of the extension tip 130 and that is in direct contact with bodily tissue 190.

Figure 2A:
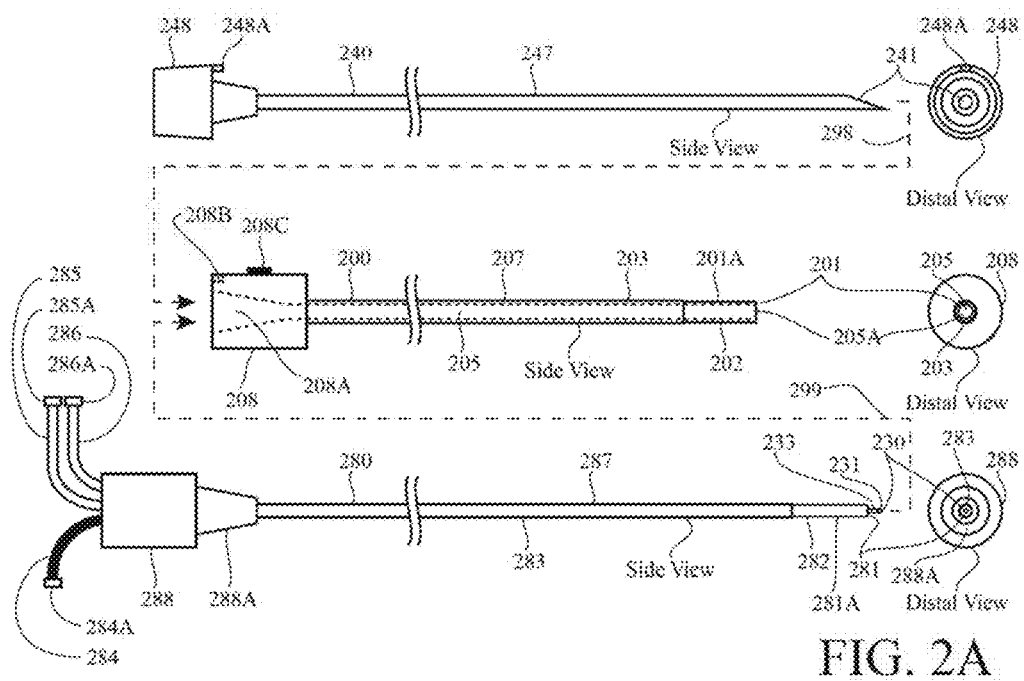
FIG. 2A is a schematic diagram showings a bipolar cooled RF system including an internally-cooled RF electrode 280, a straight introducer cannula 200, and a tissue-piercing extension stylet 240 each having a distal tissue-penetrating end and a proximal non-tissue-penetrating end, wherein the cannula 200 includes electrically-conductive active tip 201A at its distal end and electrically-insulative shaft portion 203 at its proximal end; the electrode 280 includes electrically-conductive active tip 281A at its distal end and electrically-insulative shaft portion 283 at its proximal end; the assembly of the extension stylet 240 and cannula 200 can be used to pierce bodily tissue 190 to create a track, and the electrode 280 can replace the stylet 240 within the cannula lumen 205 and be advanced into the tissue 190 through the track so that the electrode active tip 281A is separated from cannula active tip 201A by a length S of the electrically-insulative electrode shaft portion 283; the electrode 280 includes and extension temperature sensor 231 forming the distal external surface of coaxial shaft 230 extending distally from the active tip 281A of the electrode 280 that is; the electrode 280 and cables 284 and 274 electrically isolate the coaxial satellite temperature sensor 231, the electrode active tip 281A, and cannula active tip 201A when the electrode 280 and cannula 200 are assembled; the electrode 280 thermally isolates the temperature sensor 231 from coolant within the electrode 280; the electrode cable 284 conducts a first RF potential to the electrode active tip 281A, a second RF potential to the cannula active tip 201A via engagement of the electrically-conductive electrode hub taper 288A and the electrically-conductive cannula hub port 208A, and temperature signals from the temperature sensor 231; the outer surface of electrode hub 288 and the outer surface of cannula hub 208 are electrically insulated so that when the electrode hub taper 288A engages with the cannula hub taper 208A, the assembled hubs of the electrode 280 and cannula 208 are substantially electrically insulated.
Figure 2B:
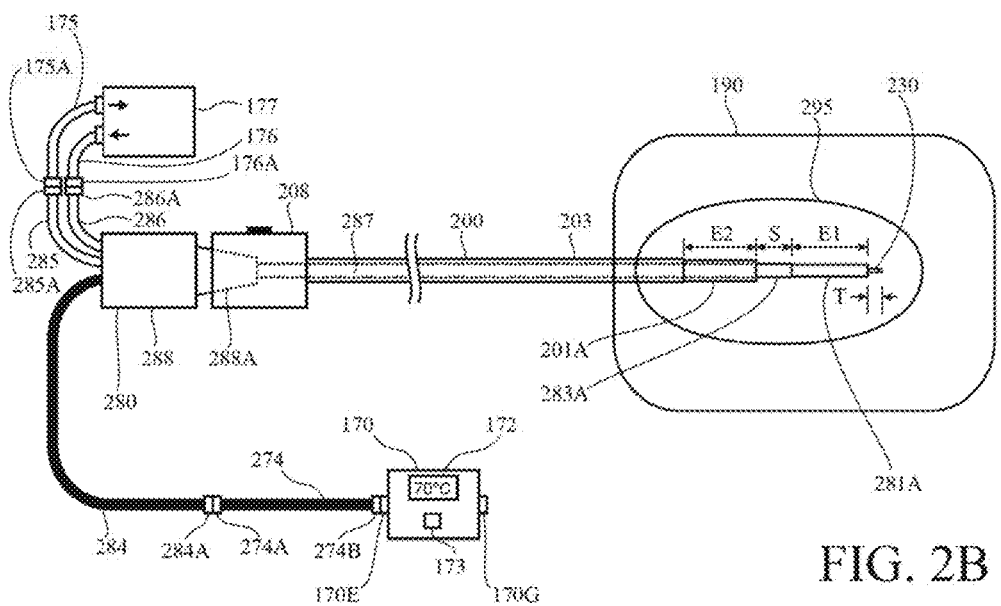
FIG. 2B is a schematic diagram showing temperature-controlled bipolar cooled RF lesioning of bodily tissue 190 by means of the assembled electrode 280 and cannula 200 of FIG. 2A, which are cooled by the flow of saline or water coolant within electrode 280 from pump 177, whose respective active tips 281A (having length E1) and 201A (having length E2) are spaced by inter-tip insulation length S and are each connected to a different RF electrical potential generated by RF generator 170, and between which RF current flows thereby raising tissue distal to electrode active tip 281A to a temperature that is sensed by the sensor 231 forming the exterior distal surface of extension temperature-sensor shaft 230 of electrode 280 and that is controlled by generator 170.
Figure 2C:
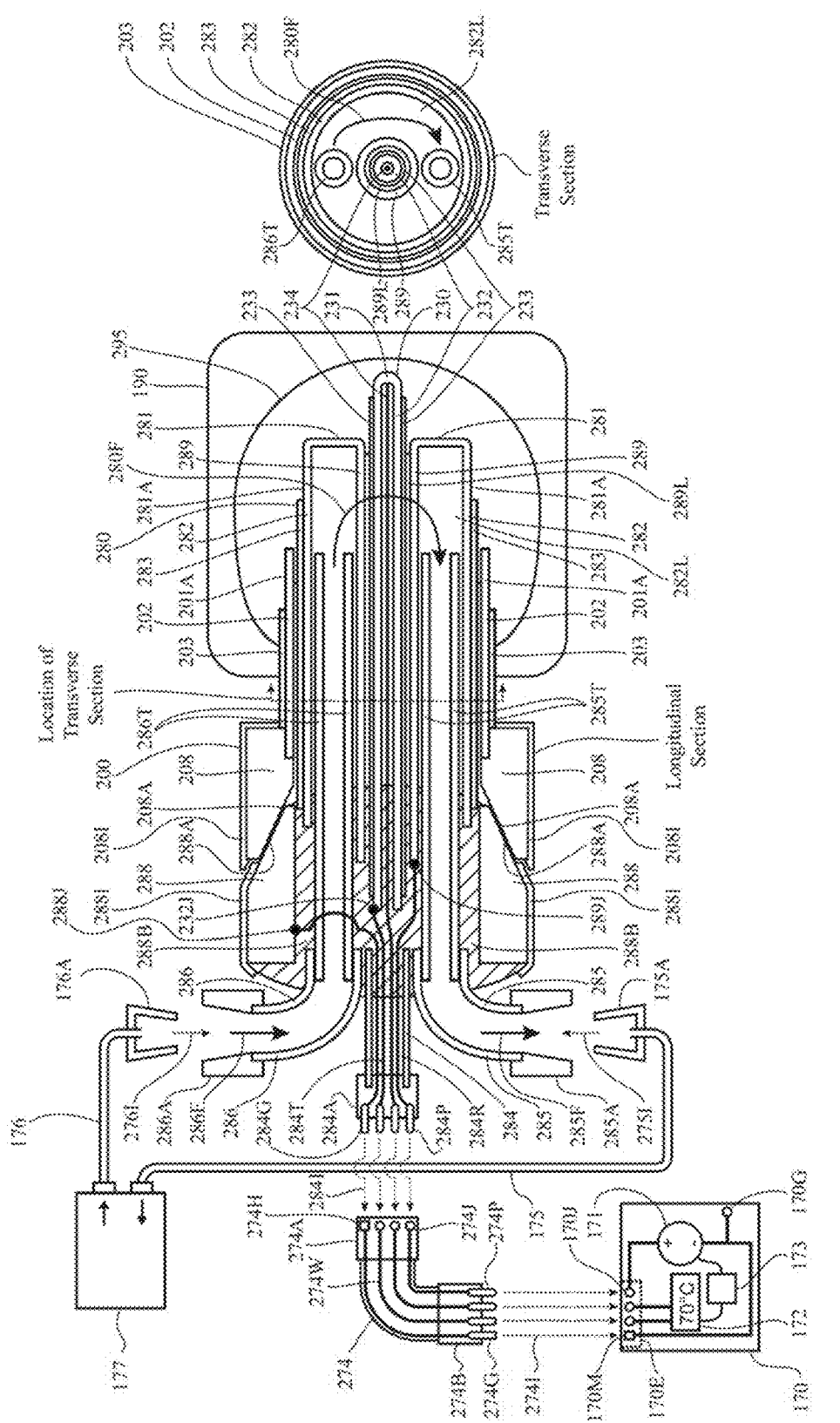
FIG. 2C is a schematic diagram showing one embodiment of the construction of the operating temperature-controlled, bipolar, cooled RF system shown in FIG. 2B, in which the electrode 280, cannula 200, tubes 176 and 175, and generator cable 274 are shown in cross-sectional views; in which the electrode conducts a reference RF potential from generator jack 170M to the cannula active tip 201A via physical contact between the electrically-conductive hub taper 288A of the electrode 280 and the electrically-conductive hub port 208A of the cannula 201; in which electrical insulation 2881 covers a portion of the electrode hub 288, and electrical insulation 2081 covers a portion of the cannula hub 208, such that the assembled electrode and cannula hubs are insulated to touch from the outside; in which the satellite thermocouple temperature sensor 231 forms the distal surface of distal extension shaft 230 and directly contacts bodily tissue 190 to rapidly and accurately measure adjacent tissue temperature; in which the system electrically isolates the temperature sensor 231 from RF potentials generated by RF supply 171 in generator 170 by means of electrical insulation and open spacing 289L between conductive elements carrying temperature-sensor signals and conductive elements carrying RF potentials, thereby reducing bias in the tissue temperature measurement by sensor 231 by limiting delivery of RF output from the metallic thermocouple sensor 231 to tissue 190, and thereby limiting direct joule heating of nearby tissue; and in which the satellite temperature sensor shaft 230 includes a stiff metal tube 232, is separated from the from inner tube 289 of the electrode shaft 287 by a plastic layer 233 and a physical gap 289L, and is anchored to the electrode only within the electrode hub 288 by glue 288B so that the temperature sensor 231 has a fixed location relative to the electrode active tip 281A, is stiff and robust to movement of the electrode 280 within solid tissue 190, and is thermally insulated from the rest of the electrode 280 and the coolant flow 280F within the electrode, thereby reducing bias in the tissue temperature measurement by sensor 231 due to thermal conduction along the satellite temperature-sensor shaft 230.

Referring now to FIG. 2, in accordance with several aspects of the present invention, FIG. 2 refers collectively to FIG. 2A, FIG. 2B, and FIG. 2C. FIG. 2 presents schematically several embodiments of a system for coaxial bipolar cooled RF ablation including a cannula 200 having an insulated shaft 203 and an active tip 201A with square cut distal end 201, and internally-cooled RF electrode 280 that electrifies the cannula active tip 201A with a reference RF potential "−", includes an insulated shaft 283 and active tip 281A electrified with a different RF potential "+", extends distal to the cannula distal end 201 to separate and electrically-isolate the electrode active tip 281A from the cannula active tip 201A so RF current flows between the active tips 281A and 201A through bodily tissue 190 to heat the bodily tissue and form heat lesion 295, and includes an extension temperature sensor shaft 230 which is electrically, thermally, and physically separated from the electrode active tip 281A and the coolant within the electrode shaft 287. In one aspect, FIG. 2 relates to an internally-cooled RF electrode 280 that generates an RF ablation zone within bodily tissue and that provides for rapid, accurate measurement of the maximum generated tissue temperature within the ablation zone (or a temperature close to or strongly correlated with said maximum generator tissue temperature), with reduced bias from direct heating of the tissue 190 by RF current flowing through the temperature sensor 231 itself, and within reduced bias from conduction of heat between the temperature sensor 231 and the rest of the internally-cooled electrode 280. In one aspect, FIG. 2 relates to a satellite temperature sensor structure 230 that is fixedly attached to an internally-cooled RF electrode 280 in order to measure tissue temperature at a predetermined location relative to the electrode active tip 281A, that is mechanically robust to manipulations of the electrode 280 in solid bodily tissue 190, that directly contacts tissue 190 which the electrode 280 penetrates, that does not actively generate RF current capable of substantially heating the tissue 190, and that reduces thermal conduction between the temperature sensor 231 and the rest of the internally-cooled electrode 280 via the temperature sensor's support structure 232. In some aspects, FIG. 2 relates to a method of temperature-controlled bipolar cooled RF tissue ablation whereby tissue 190 at a predetermined location relative to the active tip 281A is measured and controlled by means of an electrically-passive, high-speed temperature sensor 231 that is thermally insulated from the internally-cooled portions 282L of the electrode 280. In some aspects, FIG. 2 relates to a method for using a thermocouple temperature sensor 231 to control tissue temperature at a fixed location relative to the active tip 281A of an internally-cooled RF electrode 280 with reduced bias from tissue heating due to RF current generated by the temperature sensor 231 and from heat sinking through the support structure 232 of the thermocouple 231 to the coolant within the electrode. In some aspects, FIG. 2 relates to a collinear-bipolar cooled RF ablation probe system wherein internally-cooled RF electrode 280 includes a distal extension temperature sensor 231, conducts both a first RF potential "+" to the electrode active tip 281A and a second reference RF potential "−" to the cannula active tip 201A, and cools both the active tip 281A of the electrode and the active tip 201A of the cannula; and wherein cannula 200 provides both for introduction of the electrode 280 into solid bodily tissue 190 without damaging the electrode satellite temperature sensor shaft 230, and for heating of bodily tissue 190 in concert with electrode 280 without the use of a reference ground pad 160. In some aspects, FIG. 2 relates to a collinear-bipolar RF ablation probe system which is configured for use in an MRI scanner (including the embodiments shown in FIG. 2, as well as more general range of embodiments, including embodiments in which the electrode is internally cooled, embodiments in which the electrode is not internally cooled, embodiments in which the electrode is internally cooled and includes an extension temperature shaft, embodiments in which the electrode is internally cooled and does not include an extension temperature sensor shaft, embodiments in which the system includes an electrode and a cannula, and embodiments in which the electrode operates on its own without a cannula), which conducts both a first RF potential "+" to a first active tip 281A and a second reference RF potential "−" to a second active tip 201A in order to heat bodily tissue 190 without the use of a ground pad 160, and which is composed of a minimum of MRI-safe materials and metals so that the probe system can be scanned by an MRI scanner while creating an RF heat lesion and/or while not creating an RF heat lesion, and an MRI image can be produced that shows the probe system and the bodily tissue in which the probe system is inserted.

In some embodiments, the bipolar RF electrode 280 and cannula 200 shown in FIG. 2 can have similar or the same construction, dimensions, and/or materials as the monopolar RF electrode 180 and cannula 100 shown in FIG. 1 with modifications that include the cannula 200 is configured to operate with extension stylet 240 having a flat angled sharp bevel tip 241 which is indexed to the cannula hub by stylet cap tab 248A and cannula hub tab slot 208B; cannula 200 includes both a proximal portion of the shaft covered by electrical insulation 203 and distal active tip portion 201A; cannula hub slot 208A is electrical conductive and electrically connected to conductive shaft tube 202 and active tip portion 201A; the external surfaces of cannula hub 208 and electrode hub 288 are covered by electrical insulation such that when hubs are engaged with each other, the external surface of the combined hub is electrically insulates signals within the hub from outside touch; electrode hub 288 includes conductive taper 288A that conducts the RF reference potential "−" from generator supply 171 to the cannula conductive hub port 208A and thus the cannula active tip 201A; the proximal length of electrode conductive outer tube 282 is covered by electrical insulation 283 to define distal active tip 281A connected to the RF output potential "+" from supply 171 and to prevent shorting the two poles "+" and "−" of the RF supply 171 together within the assembled electrode 280 and cannula 200; the electrode active tip 281A and cannula active tip 101A are connected to opposite poles of RF supply 171 and are separated by insulated electrode shaft length 283A so that RF current flows between the electrode active tip 281A and the cannula active tip 201A to heat tissue 190 and thereby produce a cooled RF heat lesion 295 without the use of a reference ground pad 160.

Referring now to FIG. 2A, the electrode 280, the cannula 200, and the stylet 240 are shown separately, and each is shown in both a view from the side ("Side View") and from the distal end (ie looking toward the proximal end) ("Distal View"). The inner wall of the cannula 200, including the inner wall of the hub port 208A and the inner wall of shaft tube 202, is shown in the Side View as a dashed line through the solid side walls of the hub 208 and metal shaft tub 202.

Referring now to FIG. 2B, the cannula 200 and electrode 280 are shown assembled and producing a bipolar cooled RF heat lesion 295 in bodily tissue 190 by flow of RF current between electrode active tip 281A and cannula active tip 201A through the tissue, while pump 177 circulates coolant fluid through electrode shaft 287, including through the active tip region 281A. The distal hub taper 288A and the shaft 287 of the electrode 280 are shown as dotted lines in the Side View through the solid walls of the cannula 200. Extension cable 274 and integral leader cable 284 carry the temperature signal from extension temperature sensor 230 to the generator 170, and both the RF signal output signal "+" and the RF reference signal "−" from the generator 170 to the electrode 280; electrode 280 isolates these signals from each other, conducts the RF signal output "+" to the electrode active tip 281A, and conducts that RF reference signal to the cannula active tip 201A via conductive engagement between the electrode hub taper 288A and the cannula hub port 208A. In this example, the measured and displayed temperature 172 is 70° C. In some example, the temperature can range between the coolant temperature and the maximum tissue temperature, depending on the geometry of the electrode 280 and extension temperature tip 230, generator output level, and tissue properties. In some examples the measured temperature 172 can be in the range 20 to 105° C.

The active tip length E2 of the cannula active tip 201A is equal to the active tip length E1 of the electrode active tip 281A to equalize heating between both active tips. In some embodiments, E1 and E2 and be unequal to provide for unbalanced heating between the active tips, or to compensate for enhanced cooling of the electrode active tip 281A due to closer proximity to the coolant within the electrode shaft 282. The spacing S between the electrode active tip 281A and cannula active tip 201A is configured to be large enough to prevent so much current focus in the tissue lateral to the spacing that tissue heating around the rest of the active tips is limited. In some embodiments, E1 and E2 can each be selected from range 5 mm to 30 mm. In some embodiments, each of E1 and E2 can either be less than 5 mm or greater than 30 mm. In some embodiments, the spacing S can be a value selected from a range in the list: less than 5 mm, 5 mm to 20 mm, greater than 20 mm. The length E1 of the electrode active tip 281A, the length of the cannula active tip 201A, the length S of the insulated electrode shaft length 283A between the active tips 281A and 201A can be configured to produce a substantially convex RF heat lesion 295 when the electrode 280 is internally cooled for coolant from pump 177, using a process that includes one or more method selected from the list: equalizing E1 and E2, equalizing the surface areas of the more distal active tip 281A and the more proximal active tip 201A; setting E2 larger than E1 to reduce heating at E1 to account for reduced a reduced cooling rate at E2 due to reduced thermal conduction through the cannula wall 202, electrode shaft insulation 283, and any gap in between; optimizing S relative to E1 and E2; adjusting S to distribute lesion formation along the entire length of both active tips 281A and 201A.

Referring now FIG. 2C, the system and operational bipolar cooled-RF lesioning configuration of FIG. 2B are presented in a different schematic diagram in which each of the electrode 280, cannula 200, generator 170, cable 274, cable 284, tubing connection 175A, and tubing connection 176A are shown in a cross-sectional view; the cable and tubing connections are exploded for clarity, with the connections indicated by dotted arrows 274I, 284I, 275I, and 276I; and the location of the transverse cross section ("Transverse Section") of the assembled electrode 280 and cannula 200 is indicated in the longitudinal cross-section ("Longitudinal Section") by the line labeled "Location of the Transverse Section".

Cannula 200 includes conductive stainless-steel hub body 208 which is conductivity attached to stainless steel shaft tube 102, and includes conductive port 208A. The hub body is externally covered by electrical insulation 2081, and the proximal shaft tube 102 is externally covered by tubular electrical insulation 103 to define active tip 101A.

Electrode 280 includes stainless steel outer shaft tube 282, distal annular plate 281, and inner shaft tube 289 all of which are conductively fused together at the distal end, for example by welding or soldering, to contain coolant fluid 280F within the lumen 282L between tube 282 and tube 289. One advantage of forming the distal end with flat distal plate 281 is that the distal wall thickness of fluid lumen 282L within active tip 281A can be uniformly thin to improve cooling of tissue distal to the active tip 281A. The proximal end of the fluid lumen 282L is sealed by hub glue 288B. Coolant from pump 177 enters the electrode coolant lumen 282L via inflow tubes 286 and 286T, and exits the lumen via outflow tubes 285T and 285. The proximal end of the outer electrode shaft 282 is covered externally by electrical insulation 283 thereby preventing a short circuit between cannula active tip 201A and electrode active tip 281A. The electrode hub includes stainless steel hub body 288 which is covered by electrical insulation 2881 externally, and electrically-insulative rigid glue 288B that holds together much of the electrode structure and electrically isolates conductive elements within the hub, including those carrying the RF reference signal "−", the RF output signal "+", and the thermocouple (TC) signals. For example, glue 288 separates the conductive hub body 288 at RF reference potential from the conductive electrode outer shaft tube 202. Satellite temperature sensor shaft 230 is fixedly anchored to the rest of the electrode 280 structure, including the electrode active tip 281A, by hub glue 288B. Satellite TC shaft 230 includes thermocouple weld 231 between stainless steel shaft tube 232 and insulated constantan wire 234, and electrical and thermal insulation 233 to electrically and thermally insulate the extension temperature sensor 231 from the coolant flow 280F within the electrode lumen 282L. Cables 274 and 284 include four electrically-insulated wires, a first wire carrying the RF reference potential "−" from jack 170M to conductive hub body 288 via conductive junction 288J, a second wire carrying RF signal output potential from the "+" pole of RF supply 171 to the electrode active tip 181A via conductive junction 289J and inner shaft tube 289, a third wire connecting a first input of the generator temperature measurement circuit 172 to insulated constantan wire 234, and a fourth wire connecting a second input of the generator temperature measurement circuit 172 to the stainless steel shaft 132 of the extension TC shaft 130 via conductive junction 232J. Physical contact between the taper 288A of electrode conductive hub body 288 and port 208A of cannula conductive hub body 208 conducts the RF reference potential "−" of RF supply 171 to cannula conductive shaft tube 202 and its active tip portion 201A.

One important advantage of electrode hub glue 288B, electrode hub 288, and cannula hub 208 is that they provides for a simple and compact assembly of the internally-cooled electrode-cannula ablation probe system 280 and 200, and electrical isolation of conductive element therein, thereby allowing the dimension and weight of the hub 288 and the whole probe system 280 and 200 to be reduced. Reduction of the dimension and weight of the hub 288 and the whole probe system 280 and 200 has advantages, including facilitating use of the electrode 180 in the bore of an MRI scanner, facilitating use of the electrode 180 in the small bore of an high-field-strength MRI scanner, reducing the likelihood of the electrode being displaced by the hub weight for more shallow insertions of the electrode shaft 187 into bodily tissue 190, allowing for close spacing of multiple electrode 180 for the purpose of clustered RF lesioning or inter-electrode bipolar RF lesioning. The weight of the hubs 208 and 288 can be further reduced by minimizing the amount of metal material (such as metallic hub bodies 208 and 288) within the hubs.

In some embodiments, the electrode shaft insulation 283 can be configured to enhance thermal conduction (for example, by selecting a material with high thermal conductivity or by reducing the wall thickness while preserving electrical insulation characteristics) and thereby to enhance cooling of tissue nearby the cannula active tip 201A by coolant fluid 280F within electrode shaft lumen 282L. In some embodiments, the gap between the electrode shaft insulation 283 and the inner wall of the cannula shaft tube 202 can be reduced to enhance cooling of tissue nearby the cannula active tip 201A by coolant fluid 280F within electrode shaft lumen 282L. In some embodiments, the more-proximal active tip (which in FIG. 2 is the cannula active tip 201A) can be directly integrated into the electrode 280, for example by adding a conductive ring over the electrode shaft insulation 283 (for example, by swaging) and wiring said ring to electrode cable pin 284G (and thus to generator reference-potential jack 170M), thereby creating a one-piece collinear bipolar cooled RF probe.

In some embodiments, different types of conductive structures within electrode hub 288 and cannula hub 208 can conduct the generator reference potential "−" to the cannula active tip 201A, including gold, silver, titanium, platinum, MRI-safe metals, metals other than stainless steel, pins, tabs, jacks, and slots. In some embodiments, the reference potential "−" can be directly connected to the cannula shaft by an additional generator cable, rather than through conductive mating of the electrode and cannula hubs. In some embodiments, the volume of the conductive metallic interface contacts 288A and 208A can be reduced, for example, the contacts can be metallic plates, pins, jacks, or metallic coatings on hub bodies 288 and 208. In some embodiments, the conductive contacts 288A and 208A can be reduced in volume and constructed from an MRI-safe metal to minimize imaging artifacts in MRI imaging of the probe.

In some embodiments, conductive structures of the electrode 280, cannula 200, and cable 274, and other components can be minimized in volume and composed of "MRI-safe" non-ferromagnetic alloys, such as titanium, to provide for use within an MRI scanner with minimized imaging artifact and MRI-induced heating and forces. For example, the shaft outflow tube 285T can be shortened to reduce metal content (including shortened as to not enter the electrode shaft lumen 282L, but rather terminate in a lumen within the hub 288, as shown by outflow tube 585T in lumen 588D of hub 588 of electrode 580 in FIG. 5), the shaft outflow tube 585T can be a plastic tube, and/or the shaft inflow tube 286T can be a plastic tube (such as a thin wall polyimide tube). In addition, a filter can be applied to the RF outputs of generator 170, including generator supply 171, to reduce output-signal frequencies that interfere with MRI scanning Such MRI-compatible embodiments of the collinear bipolar RF system of FIG. 2 (or a similar system omitting internal cooling, or a similar but more simple system including a temperature sensor within the electrode shaft 287 rather than on an extension shaft 230, or similar one-piece system that integrated electrode 280 and cannula 200) has the advantage of limiting the number of cables from RF generator 170 (which, in some embodiments, is positioned outside the MRI scanner suite) approaching or entering the MRI scanner, omitting the use of reference ground pads (eg pad 160) within or near the MRI scanner, and thereby enabling RF ablation to proceed during as MRI scanning with less risk of induced heating in cables and ground pads. This includes either RF ablation output delivery simultaneously with MRI scanning, or RF ablation output delivery rapidly interleaved in time with MRI scanning so that RF is not delivered at the same time as MRI scanning antenna are active. This has the advantage of enabling real-time 3D temperature monitoring of tissue heated by the bipolar cooled RF system of FIG. 2, using MRI thermometry scanning sequences. In some examples, this embodiment can be advantageous for RF lesioning of brain tissue for treatment of movement disorders of epilepsy where it can be important to monitoring the three-dimensional distribution of temperature around an ablation probe in real time as the heated temperature distribution changes both to assess completion of ablation and to avoid damaging nearby sensitive structures. In some examples, this embodiment can be advantageous for RF lesioning of a tumor (for example in an organ such as the liver, kidneys, pancreas, lung, adrenal glands, bone, vertebra, brain, and other bodily organs) to assess ablation margins and to avoid damage to nearby sensitive structures (such as nerves, blood vessels, ducts, skin, tissue-interfaces, organ interfaces, bodily cavity walls) which are desirable to preserve without damage from the RF heat lesioning process.

In some embodiments, the system of FIG. 2 can additionally include ground pad 160 attached to reference jack 170G and placed on the surface of body 190, and generator 170 can be additionally configured with switches and automatic controller 173 to provide for arbitrary sequences of connections from RF potentials "+" and "−" of supply 171 to the ground pad 160, electrode active tip 281A, and cannula active tip 201A, including both rapidly-repeating sequences and non-repeating sequences, including one of more polarities selected from the list: monopolar E1 with E2 disconnected, monopolar E2 with E1 disconnected, monopolar E1 and E2 connected to the same potential at the same time, bipolar between E1 and E2, ground pad connected to the same potential as the hotter of E1 and E2, wherein E1 and E2 connected to opposite RF potentials, in order to equalize the temperatures of E1 and E2 in predominantly bipolar operations.

In some embodiments, the system of FIG. 2 can be additionally include ground pad 160 attached to reference jack 170G and placed on the surface of body 190, and a modified version of the cable 274 can leave reference jack 170M disconnected by omitting pin 274G, and can connect the RF output potential, the RF output jack 170J, pin 274P to both cable jack 274J and cable jack 274H thereby bringing both the electrode active tip 281A and the generator active tip 201A to the RF output potential. As such, in this two-active-tip collinear monopolar configuration, RF current flows through bodily tissue 190 from both the electrode active tip 281A and the generator active tip 201A to the ground pad 160, and an RF heat lesion forms around both tips with less focusing of current between the active tips than a collinear bipolar configuration.

In some embodiments of generator 170, the generator can include a current measurement device for each jack 170G, 170M, 170J connected to an RF potential generated by RF supply 171, so that for each jack 170G, 170M, and 170J, the current flowing through the jack can be measured and used as an input for the generator automatic controller 173 and user-display 172. In some embodiments, the generator 170 can use this current information to automatically distinguish a bipolar configuration (which is indicated when current flows through cannula active tip jack 170M and electrode active tip jack 170J, with no current flowing through ground pad jack 170G, eg FIG. 2) from a monopolar configuration (which is indicated when current flows through ground pad jack 170G and electrode active tip jack 170J, with no current flowing through second-electrode jack 170M, eg FIG. 1) from a tripolar configuration in which each of two active tips (eg electrode active tip 281A and cannula active tip 201A) and at least one ground pad 160 are connected to one of two RF potentials at the same time (which is indicated when current flows through jacks 170G, 170J, and 170M at the same time), and then accordingly adjust the RF output level, switched connections between output jacks and the RF power supply 171, output settings, measurement levels triggering cut-off of the RF output to some or all of output jacks, and/or user displays. In some embodiments, the generator can prompt the user to select among tripolar configurations including "monopolar cluster" in which two active tips at the same electrical potential are referenced to one or more ground pads, and "monopolar-bipolar" in which the first active tip is connected to a first RF potential, and the second active tip and the ground pad are both connected to a second RF potential. This method includes automatic detection of electrode and ground pad connections by measurement of current flow through each connection individually, and adjusting the generator configuration based on the detected connections, and can be generalized to the case of more than one active tip jack (either on a single probe structure, or on more than one than one physically-separate probe structures) and/or of more than one ground pad jack.

Figure 3:
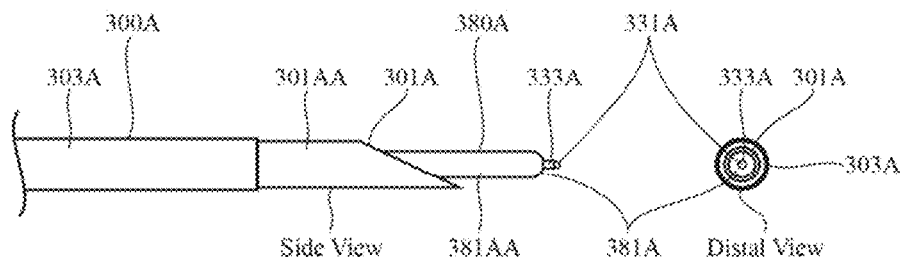
FIG. 3 is a schematic diagram showing alternative embodiments of the distal end of the coaxial-satellite-temperature-controlled monopolar cooled RF electrode-cannula system of FIG. 1, including hemispherical electrode distal end point 381A; bullet-shaped electrode distal end point 381B; cannula 300A including at its distal end a sharp, flat, angled bevel 301A, and an electrically-conductive active tip 301AA (that includes bevel 301A) that is electrified by the electrode 380A within the cannula lumen and that forms a combined active tip along with the portion 381AA of the electrically-conductive electrode shaft that extends distal to the cannula distal end; cannula 300B including a square-cut distal end with sharp distal taper 301B, and an electrically-conductive active tip 301BA (that includes taper 301B) that is electrified by the electrode 380B within the cannula lumen and that forms a combined active tip along with the portion 381BA of the electrically-conductive electrode shaft that extends distal to the cannula distal end; electrode 380C having distal end 381C that aligns with the distal end of cannula 300C and that forms a combined active tip 381CA and 301CA when fully inserted into the lumen of cannula 300C, which includes a conductive active tip 301CA that includes sharp flat bevel 301C; and electrode 380D having flat distal end point 381D that aligns with the distal end 301D of fully-electrically-insulated cannula 300D thereby conducting current to bodily tissue only through the flat distal face of the assembled electrode 380D and cannula 300D, and generating a heat lesion in bodily tissue substantially distal to the electrode-cannula assembly.
Figure 3:
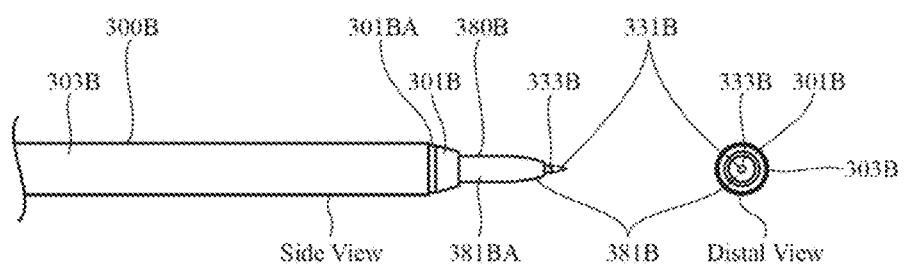
Figure 3:
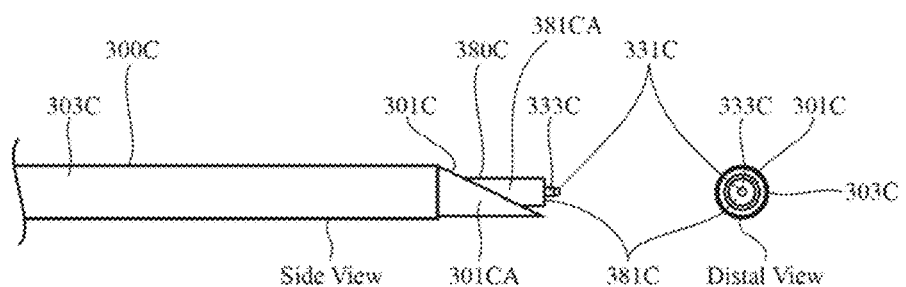
Figure 3:
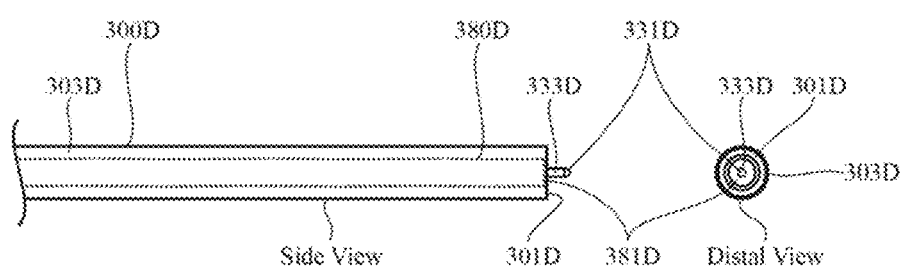

Referring now to FIG. 3, in accordance with several aspects of the present invention, FIG. 3 presents schematically several embodiments of the distal end of partially- or fully-insulated cannulae 300A, 300B, 300C, 300D and internally-cooled RF electrodes 380A, 380B, 380C, 380D, wherein each electrode can be inserted into bodily tissue through a cannula, and each electrode includes an distal extension shaft having a proximal electrically-insulated portion 333A, 333B, 333C, 333D and a distal temperature sensor 331A, 331B, 331C, 331D that is be electrically, thermally, and physically separated from the electrode active tip 381AA, 381BA, 381CA, 381DA and the coolant within the electrode shaft, respectively. Cannula embodiments include 300A, 300B, 300C, and 300D. Electrode embodiments include 380A, 380B, 380C, and 380D. Each electrode embodiment is shown fully inserted into a cannula embodiment, in an external view both from the side ("Side View") and from the distal end ("Distal View").

Cannula 300A, 300B, and 300C each include a conductive active tip region 301AA, 301BA, and 301CA, respectively, that is electrified and brought to the same electrical potential as the electrode active tip region 381AA, 381BA, and 381CA, respectively, by contact between the exterior surface of the conductive electrode shaft tube and the interior surface of the conductive cannula shaft tube that forms the cannula active tip. As such, each of the assembled electrode-cannula probes 380A-300A, 380B-300B, and 380C-300C include a combined active tip formed from the combination of the electrode active tip and cannula active tip. Providing a variety of cannula having active tips with a variety of lengths for use with an electrode in assemblies similar to those of assembled electrode-cannula probes 380A-300A, 380B-300B, and 380C-300C, has the advantage that a single internally-cooled electrode including an extension temperature sensor tip can be used with one of a variety of more simple cannulae to achieve a variety of RF lesion sizes to suit clinical needs. In the assembly of cannula 300C and electrode 380C, the distal end 381C of active tip 381CA is substantially aligned with the distal point of cannula bevel 301C to form a substantially cylindrical combined active tip.

The active tip 300AA of cannula 300A includes a flat, angled distal bevel 301A. The active tip 301BA of cannula 300B includes a square-cut distal end including a distal taper 301B to a sharpened distal edge. The active tip 300CA of cannula 300C includes a flat, angled distal bevel 301C over substantially the entire length of the active tip 300CA. Cannula 300D has a square-cut distal end 301D and is fully electrically insulated along it shaft 303D and over its distal end 301D.

The active tip 381AA of electrode 380A includes a hemispherical distal end point 381A. The active tip 381BA of electrode 380B includes a bullet-shaped distal end point 381B. Hemispherical distal end 381A, bullet-shaped distal end point 381B, a conical distal end point, and other tapered distal end points have the advantage that they facilitate penetration of solid bodily tissue. Another advantage of a tapered electrode active tip distal end point is that it can be combined with a temperature-sensor shaft having a sharped or tapered distal end point (eg point 331B of temperature-sensor shaft 330B) to facilitate penetration and piercing of solid bodily tissue, in some embodiments. The active tip 381CA of electrode 380C includes a flat distal end point 381C. The electrode 380D includes a flat distal end surface 381D.

The metallic thermocouple weld 331B is conically sharpened so that the thermocouple extension shaft 330B can pierce solid tissue into which electrode 380B is inserted. The thermocouple weld 331B is sharpened, is formed on the end of a stiff metallic shaft (similar to shaft 130 for thermocouple 131), directly contacts bodily tissue in which the electrode 380B is positioned, is electrically insulated from active tip 381BA, and is thermally insulated from coolant within the electrode 380. One advantage of thermocouple 331B is that it can accurately and rapidly measure temperature distal to electrode active tip 380BA of an electrode 380 configured to penetrate into, and be repositioned and manipulated in, solid bodily tissue 190. The ability to sharpen extension a temperature sensor 331B that is formed at the end of a metallic shaft and that is in direct contact with bodily tissue is one advantage of using a thermocouple-type extension temperature sensor 331B. One advantage of the combination of sharpened extension thermocouple 331B and bullet-shaped electrode active tip 331BA is that it provides for robust, rapid, and accurate temperature control of cooled-RF lesioning at a depth within solid bodily tissue. In some embodiments, electrode 380B can be tissue piercing. In some embodiments, electrical insulation can be directly applied to the shaft of electrode 380B to define an active tip (just as electrical insulation 283 is applied to shaft 282 of electrode 280 to define active tip 281A, and just as electrical insulation 583 is applied to shaft 582 of electrode 580 to define active tip 581A), and electrode 380B can be inserted directly into bodily tissue without use of cannula 300B.

The electrode 380D includes flat distal end 381D which is the entirety of the conductive portion of the shaft of electrode 380D that contacts bodily tissue when electrode 380D is fully inserted into fully-electrically-insulated cannula 300D, and thus the electrode distal end 381D is the entirety of the active tip of the assembly of electrode 380D and cannula 300D. This assembly configuration has the advantage that the RF current flows into tissue only from the distal end 381D of the electrode-cannula probe assembly, thereby generating a heat lesion that is substantially only distal to the probe assembly, as can be useful for point-on approaches to bodily structures targeted for tissue ablation, such as medial branch nerves in the spine. In some embodiments, the cannula distal end 301D includes the distal end of a conductive metal tube that is fully covered by electrical insulation 303D except for its distal end 301D; in that case, the cannula distal end is part of the assembled combined active tip.

In some embodiments, the distal-end geometries of the cannulae shown in FIG. 3 can be used as alternative distal-end geometries for the cannulae shown in the other figures, including in both of monopolar probe systems. (eg cannula 100) and collinear bipolar probe systems (eg cannula 200). In some embodiments, the distal-end geometries of the electrodes shown in FIG. 3 can be used as alternative distal-end geometries for the electrodes shown in the other figures, including in both of monopolar probe systems. (eg electrode 180) and collinear bipolar probe systems (eg electrode 280).

Figure 4:
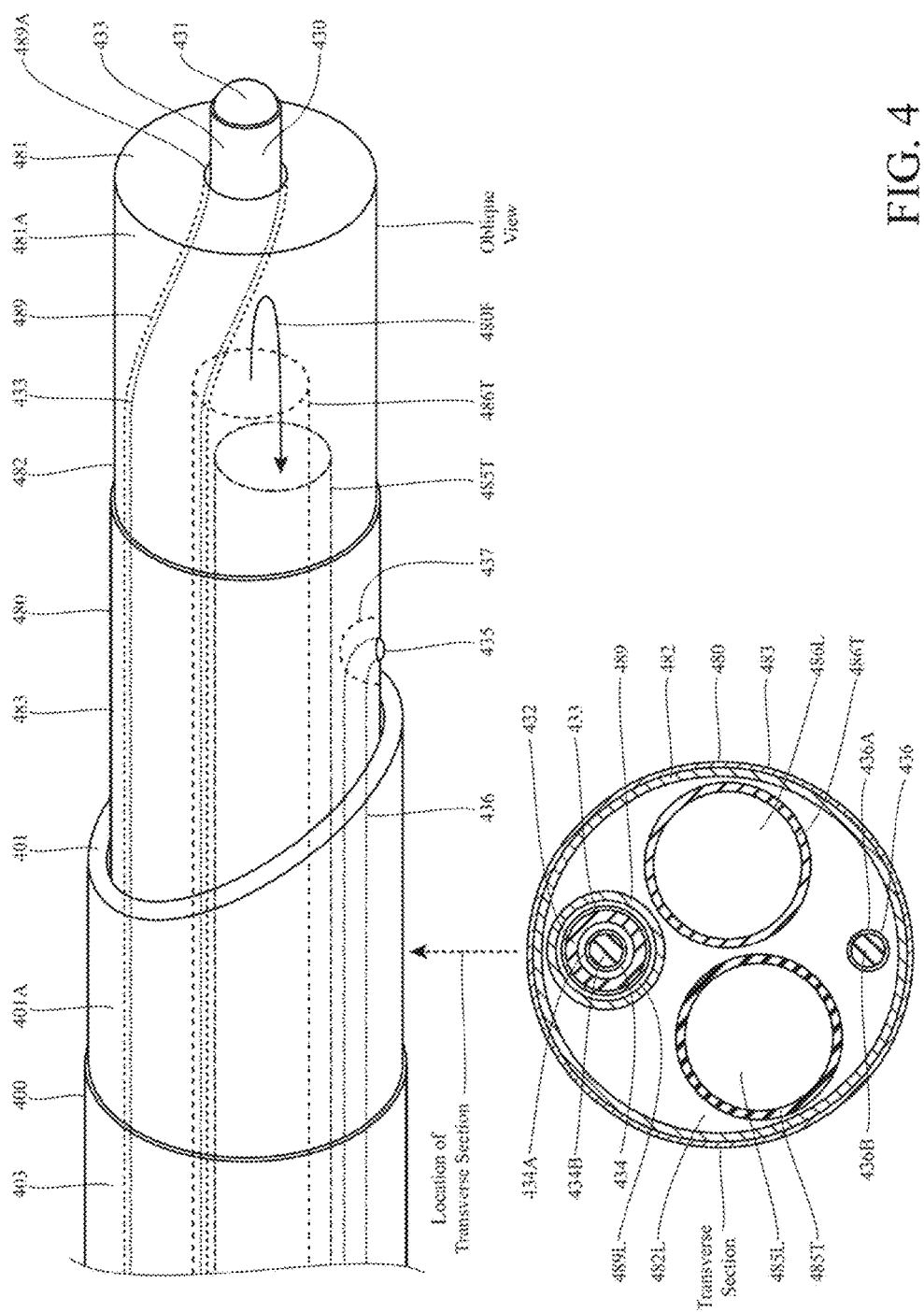
FIG. 4 is a schematic diagram showing in a coaxial-bipolar cooled RF electrode-cannula probe including a cannula active tip with a sharp flat distal bevel 401, a flat-front electrode active tip 481A, a distal satellite temperature sensor 431 that is configured to directly contact bodily tissue distal to the probe and that is electrically, thermally, physically separated from the probe active tips (401A and 481A) and coolant flow 480F within the electrode 480, and a second temperature sensor 435 located at the external surface of the electrode between the electrode active tip 481A and the cannula active tip 401A.

Referring now to FIG. 4, in accordance with several aspects of the present invention, FIG. 4 presents schematically several embodiments of a collinear bipolar internally-cooled electrosurgical ablation probe system including cannula 400 having insulated shaft 403 and active tip 401A with flat sharp angled distal bevel 401 electrified by a first RF potential, and internally-cooled RF electrode 480 that includes an insulated shaft 483 and active tip 481A (which includes a flat fluid-sealed distal end 481) electrified by a second RF potential. Electrode 480 extends distal to the cannula distal end 401 to separate and electrically-isolate the electrode active tip 481A from the cannula active tip 401A so RF current flows between the active tips 481A and 401A through bodily tissue to heat the bodily tissue and form heat lesion. Electrode 480 includes an inter-tip temperature sensor 435 in its exterior wall between the electrode active tip 481A and the cannula active tip 401A, and an extension temperature sensor shaft 430 which is electrically, thermally, and physically separated from the electrode active tip 481A and the coolant 480F within the lumen 482L between the electrode outer shaft tube 482 and inner shaft tube 489. FIG. 4 shows the distal end of the assembled electrode 480 and cannula 400, with the electrode 480 fully inserted into the cannula 400, in an oblique projection view ("Oblique View") and in a transverse cross-sectional view ("Transverse View") located at the position along the assembled probe shaft indicated by the arrow labeled "Location of Transverse Section". Structures within the electrode 480 are shown as various type of broken lines through the solid walls of the electrode 480 and cannula 400.

Referring now to the Oblique View of FIG. 4, the satellite temperature shaft 430 protrudes out of the temperature-sensor lumen 489L within tube 489 from hole 489A in the flat electrode distal face 481. The satellite shaft 430 includes metallic thermocouple temperature sensor 431 at the outer surface of its distal point, and is covered by electrical insulation 433 over its stainless steel shaft 482. Within the electrode 480, the satellite TC shaft 430 covered by insulation 433 is shown a dotted line within the lumen of the inner shaft tube 489 (dashed line), which is deflected from the central axis of the electrode shaft by the shaft inflow tube 486T (dotted line) and shaft outflow tube 485T (dash-dot line) whose open cross-sectional areas 486L and 485L are enlarged and equalized to increase coolant fluid flow (shown by arrow 480F) and thus increase cooling of heated tissue in contact with the active tip 481A. Within the electrode 480, electrically-insulated constantan wire 436 (dotted line) is welded to the stainless steel electrode shaft outer tube 482 to form inter-tip thermocouple weld 435, which is directly exposed to tissue through a hole in electrical insulation 433. Glue 437 (dotted line) within shaft tube 482 anchors wire 436 and thermally insulates and physically separates the temperature sensor 435 from coolant 480F within the lumen 482L of tube 482. In some embodiments, weld 435 can be under electrical insulation 433 to simplify manufacturing. In some embodiments, wire 436 can be a thermocouple bifilar whose two leads are welded to form thermocouple 435 that is threaded through a hole in the electrode outer shaft tube 482 and anchored to the shaft tube 482 by glue 437. The wire 436 is electrically isolated within the electrode and cables and connected to a second thermocouple measurement circuit within generator 170.

In some embodiments the cannula bevel 401 can be short in the longitudinal direction of the cannula shaft axis (for example forming an acute angle greater than 30 degrees, 45 degrees, or 60 degrees relative to the longitudinal axis) so that the spacing between the proximal active tip 401A and the distal active tip 481A is more uniform. In some embodiments, electrode 480 can operate as a monopolar electrode, as in the systems of FIGS. 1, 5, 6, 7, and 8. In some embodiments, active tip 401A can be integrated into electrode 480, for example, by permanently attaching cannula 400 and 480, or by omitting cannula 400 and adding a ring electrode over the electrode insulation 483 and wiring said ring electrode to the reference potential of the RF output delivered to active tip 481A.

Referring now to the Transverse View of FIG. 4, electrode insulation 433 externally covers outer shaft tube 482, which is physically connected to inner shaft tube 489 via distal end plate 481. Inflow tube 486T, outflow tube 485T, insulated constantan wire 436, and coolant fluid flow 480F are within coolant lumen 482L between inner shaft tube 482 and inner shaft tube 489. Insulated constantan wire 436 includes electrical insulation 436A coating the exterior surface of constantan wire 436B in order to prevent a short circuit between the outer shaft tube 482 and the constantan wire 436B except at weld 435. The cross-sectional areas of lumens 485L and 486L of tubes 485 and 486, respectively, are equal and substantially maximized within the cross-sectional area of lumen 482L in order to maximize fluid coolant flow. In some embodiments, the shaft outflow tube 485T can be omitted so that coolant fluid 480F flows out through lumen 482L, and the open cross section of the shaft inflow tube 486T can be increased and equalized to the open cross sections of lumen 182L to maximize cooling of the electrode 480 shaft and nearby tissue. Within the temperature-sensor lumen 489L of inner shaft tube 489 is satellite thermocouple (TC) shaft 430 comprising electrical insulation 433 covering stainless steel tube 432, within whose lumen is insulated constantan wire 434. Insulated constantan wire 434 includes electrical insulation 434A coating the exterior surface of constantan wire 434B. As such, the satellite thermocouple structure 430 is physically separated from coolant 480F within lumen 482 by at least three barriers along some or all of the distal electrode shaft length, namely inner tube 489, open space within the temperature-sensor lumen 489L, and electrical insulation 433. This has the advantage of electrically and thermal insulating the temperature-sensor shaft from the RF potential of the active tip 481A and the temperature of the coolant 480F within the electrode 480.

Figure 5:
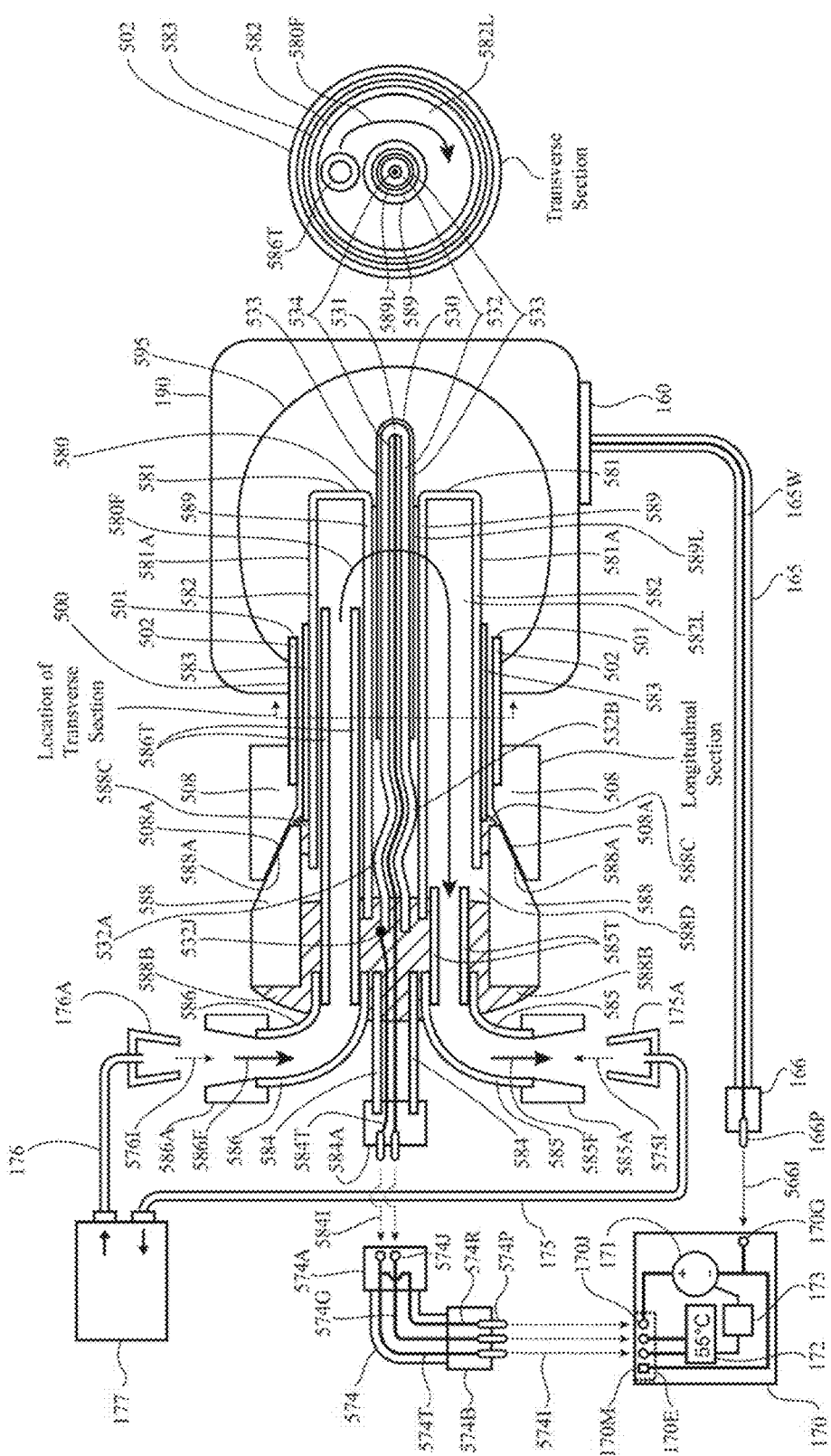
FIG. 5 is a schematic diagram showing some alternative constructions of the monopolar cooled RF electrode system of FIG. 1, in which electrode 580 includes electrical insulation 583 over the proximal portion of its metallic shaft tubing 582 to define a distal conductive active tip 581A; electrode 580 includes only an inflow tube 586T in its shaft 587 so that the shaft lumen 587L between outer shaft tube 582 and inner shaft tube 589 carries coolant flowing in through inflow tube 586T back out of the shaft 587, into the hub lumen 588D, and out through hub outflow tube 585T; extension temperature sensor shaft 530 is anchored to the rest of electrode 580 by proximal hub glue 588B; generator extension cable 574 connects both the RF-output-potential jack 170J and one pole of the thermocouple measurement circuit 172 to stainless steel tube 532 of the extension temperature sensor shaft 530; thermocouple tube 532 includes two bends 532A and 532B in opposite directions whose compression maintains contact between metallic tube 532 and the inner metallic tube 589 of electrode shaft 587, thereby conducting the RF potential from generator jack 170J to the electrode active tip 581A; electrical insulation 533 covers the distal outer surface of metal shaft 532 thereby preventing outflow of RF current from the extension temperature sensor shaft 530 and from its thermocouple 531; thermocouple 531 is formed from a weld between stainless steel tube 532 and electrically-insulated constantan wire 534 within it; thermocouple 531 is thermally insulated from coolant flow 580T within electrode shaft 587 by the gap 589L between electrode shaft inner tube 589 and the thermocouple temperature shaft 530.

Referring now to FIG. 5, in accordance with several aspects of the present invention, FIG. 5 presents schematically several embodiments of an operational monopolar cooled RF electrosurgical ablation probe system including internal cooling of the electrode 580 and a coaxial satellite temperature sensor 531 that is configured to measure tissue temperature distal to active tip 581A, without directly heating the tissue 190, and with reduced cooling of the temperature sensor 531 through the temperature sensor extension shaft 532. Each of the electrode 580, cannula 500, generator 170, cable 574, cable 584, cable 165, tubing connection 175A, and tubing connection 176A are shown in a cross-sectional view; the cable and tubing connections are exploded for clarity, with the connections indicated by dotted arrows 5741, 5841, 5751, 5761, 5661; and the location of the transverse cross section ("Transverse Section") of the assembled electrode 580 and cannula 500 is indicated in the longitudinal cross-section ("Longitudinal Section") by the line labeled "Location of the Transverse Section".

In one aspect, FIG. 5 relates to a simplified construction of a satellite thermocouple temperature probe 530 wherein all parts of the extension shaft 532 and temperature sensor 531 that extend out from an internally-cooled electrode 580 into contact with bodily tissue are fully electrically insulated by temperature-sensor shaft insulation 533, and the stainless steel side of the thermocouple 532 shares a cable wire 584T with the electrode active tip 581A in connecting to the generator thermocouple measurement circuit 172 and RF supply 171, respectively. In one aspect, FIG. 5 relates to a construction of a coolant flow path 580F within an internally-cooled electrode 580 wherein the electrode shaft 587 contains a single inflow tube 586T and outflow of coolant 580F flows through the shaft lumen 582L and a lumen 588D within electrode hub 588, thereby providing for increased coolant flow rate and lesion size 595. In one aspect, FIG. 5 relates to a construction of a cannula 500 and an electrode 580 to define a monopolar active tip 581A by applying electrical insulation 583 over the stainless steel electrode outer shaft tube 582 so that the insulation 583 extends beyond the distal end 501 of the conductive and non-electrically-insulated cannula shaft tube 502 and thereby avoids electrifying the cannula shaft tube 502 by contact with electrode active tip 581A. In some embodiments, the electrode 580, cannula 500, and cable 574 can have components, construction methods, dimensions and materials that are the same or similar to those of electrode 180, cannula 100, and cable 174, except as otherwise described herein.

Cable 574 short circuits together the wire connecting to the RF output potential "+" of generator RF power supply 171 and the wire connecting the generator thermocouple circuit 172 to the stainless steel shaft 532 of extension thermocouple 531. As such, insulated wire 584T carries both signals to the TC shaft 532 via conductive junction 532J. Conductive shaft 532 includes one or more bends 532A and 532B that ensure physical contact between shaft 532 and the inner surface of the stainless-steel electrode shaft inner tube 589, thereby conducting the RF output potential "+" to active tip 581A via welding between shaft 589, distal end plate 581, and shaft outer tube 582. Flow of RF current through the portion of the TC shaft 532 and TC weld 531 is prevented by electrical insulation 533 covering the distal end of these structures, including all parts of the temperature-sensor shaft 530 that extend out from the electrode active tip 581A into bodily tissue 190. In some embodiments, the electrical insulation 533 is applied with minimal thickness to achieve desired electrical insulation in order that temperature sensor 531 more rapidly and accurate senses tissue temperature in contact with the distal end of the temperature-sensor shaft 530. In some embodiments, the thickness of the electrical insulation proximal to the temperature sensor 531 can be increased to increase the thermal insulation the metallic shaft 532 and cooled tissue immediately distal to the active tip 581A. In some embodiments, the thickness of electrical insulation 533 can be substantially uniform. In some embodiments, insulation 533 (for example, PTFE or PET plastic) can be spray coated onto the shaft 532 and tip 531 of the temperature-sensor assembly 530. The constantan wire 534 is independently conducted to the generator TC circuit 172, which in this example measures a tip temperature of 55° C. In some embodiments, the extension thermocouple structure 532, or an analogous structure, can be used in modified embodiments of electrodes 180, 280, 380A, 380B, 380C, 380D, 480, 680, 780, and 880.

Electrode shaft coolant lumen 582L is between outer electrode shaft tube 582 and inner electrode shaft tube 589, sealed closed at its distal end by flat distal shaft end plate 581, and continuous with hub lumen 588D. Hub lumen 588D is bounded by the tubular hub body 588, distal rigid glue 588C creating a fluid-tight connection between hub 588 and electrode shaft outer conductive tube 582, and proximal rigid glue 588B creating a fluid-tight, rigid, and electrically-insulative connection among hub 588 to cable 584, tubes 586 and 585, tubes 586T and 585T, electrode shaft inner tube 589, and TC shaft 532. In some embodiments distal hub glue 588C can be replaced by overmolding hub 588 onto electrode shaft 587. Coolant from pump 177 enters the distal end of electrode shaft lumen 582L through inflow tubes 586 and 586T. Coolant flows from the distal end to the proximal end of the lumen 582L, into the hub lumen 588D, and out of the electrode 580 through tubes 585T and 585, as indicated by arrow 580F. The cross-sectional areas of the lumen of shaft inflow tube 586T and the portion of the coolant lumen 582L outside shaft inflow tube 586T can be equalized to maximize coolant flow 580F, the rate of cooling of tissue in contact with electrode 580, and the size of heat lesion 595 for a given set temperature. One advantage of electrode 580 is that coolant flow path cross-sectional area with shaft tube 582 is not consumed by the walls of outflow tube 585T, thereby increasing flow capacity. One advantage of shortening outflow tube 585T is that the electrode 580 has lower metal content and thus can product smaller distortion artifacts in CT and MRI imaging. In some embodiments, the coolant structures of electrode 580, or an analogous structure, can be used in modified embodiments of electrodes 180, 280, 380A, 380B, 380C, 380D, 480, 680, 780, and 880.

One important advantage of hub glue 588B and 588C and the construction of hub 588 is that they provide for a simple and compact assembly of the electrode 580, and electrical isolation of conductive elements therein, thereby allowing the dimension and weight of the hub 588 and the whole electrode 580 to be reduced. Reduction of the dimension and weight of the hub 588 and the whole electrode 580 has advantages, including facilitating use of the electrode 580 in the bore of an MRI scanner, facilitating use of the electrode 580 in the small bore of an high-field-strength MRI scanner, reducing the likelihood of the electrode being displaced by the hub weight for more shallow insertions of the electrode shaft 587 into bodily tissue 190, allowing for close spacing of multiple electrode 580 for the purpose of clustered RF lesioning or inter-electrode bipolar RF lesioning.

Cannula 500 includes bare stainless steel shaft tube 502. A proximal length of the outer conductive shaft tube 582 of electrode 580 is covered by electrical insulation 583 to define distal active tip 581A. When electrode 580 is fully inserted into cannula 500 such that their respective hubs 508 and 588 engage, the insulated portion 583 of electrode shaft 582 extends outside the cannula shaft lumen, thereby preventing short circuiting of the active tip 581A to the cannula shaft 502 and delivery of RF current from the cannula shaft 502 to tissue in which it is positioned. One advantage of this embodiment is that electrode 580 can be inserted into bodily tissue through a standard needle 500. Electrode shaft insulation 588, or similar electrical insulation, can be added to several modified embodiments of electrodes 180, 380A, 380B, 380C, 380D, 480, 680, 780, and 880.

As in some embodiments presented in U.S. application Ser. Nos. 14/325,295, 14/325,292, 14/325,303, and 14/325,285, in some embodiments of the present invention, distal extension tip 530 can comprise a stainless steel tube 532, a temperature sensor 531 at the distal point of the tube (for example, formed by welding a constantan wire 534 within the stainless steel tube 532 to the distal end of the stainless steel tube 532), electrical insulation 533 (which can comprise a plastic coating or sheath along the tube, and glue 588B covering wire connections 532J at the tube proximal end) entirely covering all parts of the extension tip 530 that emerge from the tip 581A and thus directly contact tissue 190; wherein the tube 530 proximal end is positioned within an inner lumen 589L of the electrode shaft 582 and tip 581A (for example, the lumen can be formed a pipe 589 within the shaft 582 and tip 581A that is welded to the distal end 581 of the pipe 582 forming the outer surface of the tip 581A, between both of which pipes (ie lumen 582L), coolant fluid flows 580F and is contained), the tube 582 position is fixed relative to the active tip 581A by a thermally-insulative element at more proximal location in the electrode 580 (for example, by glue 588B within the electrode hub 588), and the extension tip 530 is thereby thermally and physically separated from both the active tip 581A and the coolant flow 580F within the electrode shaft 582 and tip 518A, both by a physical gap 589L (ie the space between inner surface of the lumen 589L and the outer surface of the tube electrical insulation 533) and the electrical insulation 533 covering the tube 532; and wherein tube 532 can either be electrically insulated or not electrically insulated within the electrode 580 and cable 584, 784 from the HF output "+" delivered to the active tip 581A by generator 170; so that the extension tip 530 does itself produce HF heating of the tissue 190 because its outer surface is electrically insulated 533, and the extension tip 530 measures temperature of the tissue distance from the end of the active tip 581A.

Figure 6:
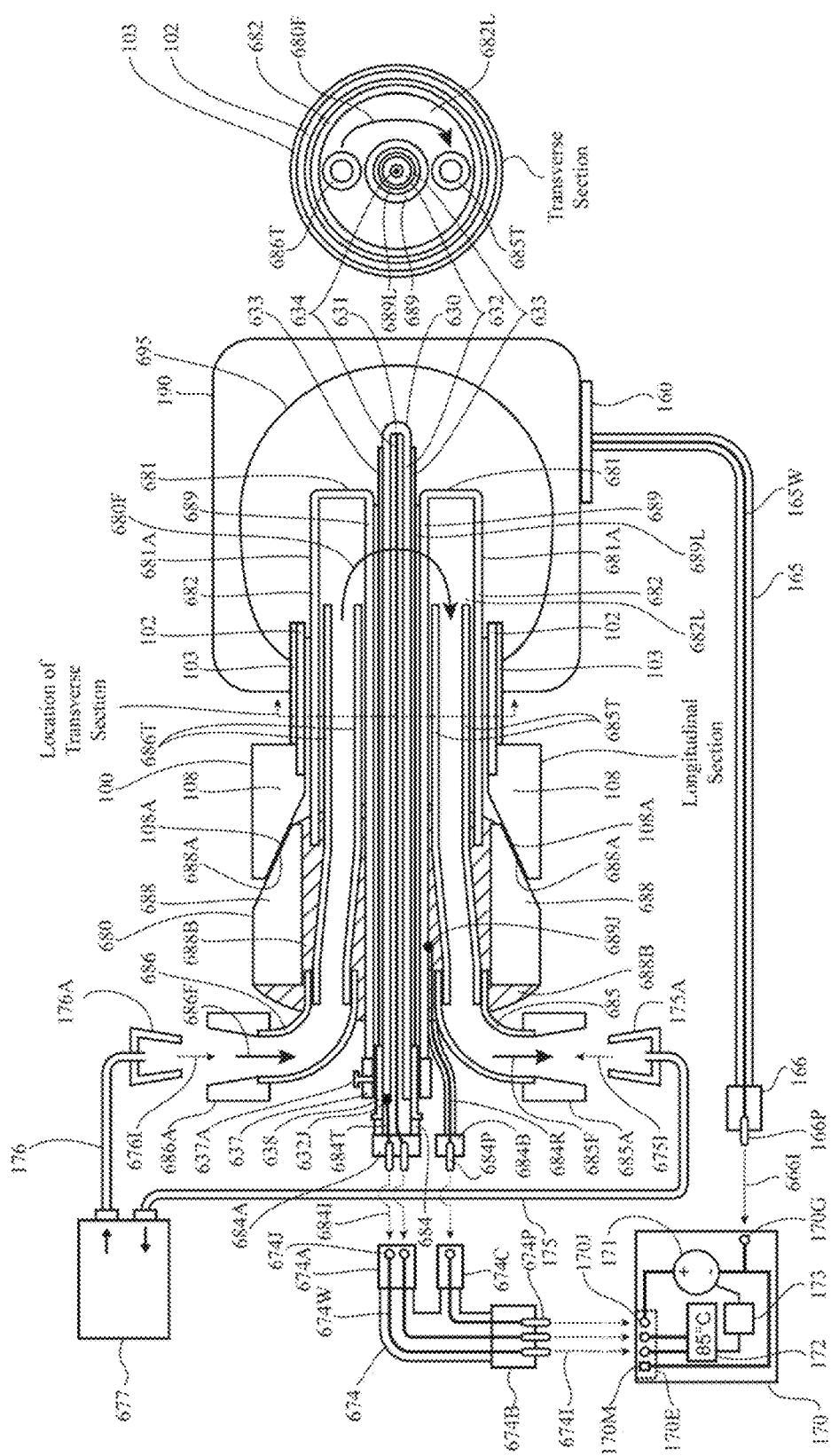
FIG. 6 is a schematic diagram showing a monopolar cooled RF ablation system including electrode 680 and movable distal extension temperature sensor 631 that can slide relative to the electrode 680 and is electrically, thermally, and physically separated from the electrode 680 by gap 689L and insulation 633.

Referring now to FIG. 6, in accordance with several aspects of the present invention, FIG. 6 presents schematically several embodiments of a monopolar cooled RF electrosurgical ablation probe system including internal cooling of the electrode 680 and a coaxial satellite temperature sensor 631 that is slidably mounted to electrode 680 and that is configured to measure tissue temperature at a user-selected location distal to active tip 681A by direct contact between the temperature sensor 631 and tissue 190, without directly heating the tissue 190, and with reduced cooling of the temperature sensor 631 through the temperature sensor extension shaft 632. Each of the electrode 680, cannula 100, generator 170, cable 674, cable 684, cable 165, tubing connector 175A, and tubing connector 176A are shown in a cross-sectional view; the cable and tubing connections are exploded for clarity, with the connections indicated by dotted arrows 674I, 684I, 675I, 676I, 666I; and the location of the transverse cross section ("Transverse Section") of the assembled electrode 680 and cannula 100 is indicated in the longitudinal cross-section ("Longitudinal Section") by the line labeled "Location of the Transverse Section". In some embodiments, the electrode 680 and cable 674 can have components, construction methods, dimensions and materials that are the same or similar to those of electrode 180 and cable 174, except as otherwise described herein.

Electrode 680 is inserted into bodily tissue 190 through fully-insulated cannula 100. Via tubes 686, 686T, 685T, and 685, coolant pump 177 circulates coolant fluid through the shaft lumen 682L which is enclosed by conductive outer shaft tube 682, flat distal plate 681, inner shaft tube 689, and electrically-insulating rigid hub glue 688B. The active tip 681A is the portion of conductive shaft 682 that can contact bodily tissue, and is the portion of shaft 682 that extends distal to the insulated cannula shaft 102, 103. The RF output signal "+" from RF supply 171 is conducted to the active tip 681A by branch 674C of cable 674, electrode leader cable wire 684R, conductive junction 689J, and inner electrode tube shaft 689. Slidable extension temperature probe 630 includes flexible generator cable 684, cylindrical hub 638, stainless steel tubular shaft 632, electrical insulation 633 covering the proximal length of shaft 632 up to (but not including) the thermocouple temperature sensor 631, thermocouple junction 631 between stainless steel tube 632 and insulated constantan wire 634, and insulated constantan wire 634. Branch 674A of cable 674 connects the generator temperature measurement circuit and display 172 to the thermocouple junction 631 via the wires, jacks, and pins of leader cable 684. Temperature probe 630 slides within the lumen 689L of inner electrode shaft tube 689, at the distal end of which is cylindrical port 637 and set screw 637A. A user can slide temperature-sensor hub 638 of temperature probe 630 within electrode port 637 to adjust the position of the temperature sensor 631 relative to active tip 681A. Set screw 637A can be tightened and loosened to constrain and release the relative positions of the thermocouple 631 and active tip 681A. An enlarged proximal portion of temperature probe hub 638 prevents the probe 630 from advancing too far distally within the tube 689. Flexible extension cable 674 includes two separate connectors 674C and 674A for the electrode 680 and temperature probe 630, respectively, to allow for free adjustment of the relative positions of the electrode 680 and temperature probe 630. Temperature probe shaft insulation 633 electrically insulates the probe 630 from the electrode inner shaft tube 689, thereby limiting RF current flow from the probe 630 into tissue 190 and direct RF heating of tissue 190 by probe 630. Probe 630 is separated from coolant flow 680F within electrode 680 by the inner shaft tube 689, gap 689L, and insulation 633. Insulation 633 covers the portion of the temperature-sensor shaft that extend out of the active tip 681A into bodily tissue 190 in order to limit thermal conduction into and along the temperature-sensor shaft from adjacent tissue, except for tissue in immediate contact with the uninsulated thermocouple 631. Thermocouple sensor 631 directly contacts tissue 190 without any intervening material to ensure an accurate and rapidly-responding temperature reading. In this example, the generator 170 registers a temperature of 85° C. measured by thermocouple 631 and displayed on display 172. One advantage of electrode 680 including a slidable temperature probe 630 is that the user can spatially map the temperature distal to the active tip 681A during RF lesioning by moving the temperature probe 680 relative to the electrode 680. One advantage of electrode 680 including a slidable temperature probe 630 is that the relative position of the temperature sensor 631 and active tip 681A can be adjusted to measure the maximum temperature of the ablation zone 695, whose location may vary depending on the RF supply 171 output level, the duration of RF output delivery, coolant temperature and flow rate, properties of tissue 190, the length of active tip 681A, the size of active tip 681A, and other generator-, time-, procedure-, application-, and patient-specific factors. One method of cooled RF heat lesioning includes positioning an cooled RF electrode 680 having a slidable coaxial temperature probe 630 within bodily tissue 190, adjusting the relative positions of the temperature probe temperature sensor 631 and the electrode active tip 681A while delivering RF output at a lower level not capable of raising any tissue temperature to a set temperature value in order to position the temperature sensor 631 at the location of maximum tissue temperature for RF output at the lower level, predicting the relative location of maximum tissue temperature for RF output at a higher level capable of raising the maximum tissue temperature to the set temperature value (which, in some embodiments, can be the same location as the location of maximum tissue temperature for RF output at the lower level), moving the temperature sensor 631 to the predicted location of maximum tissue temperature for RF output at the higher level, increasing and adjusting the RF output to control the temperature measured by temperature sensor 631 to be at or near the set temperature value. In some embodiments, electrode 680 can include a linear motor drive configured to advance and retract the temperature probe 630 relative to the active tip 681A; in some embodiments, the linear motor drive can be attached to and controlled by generator 170, either by manual user controls included in the generator user interface, or by an automated controller. In some embodiments, inner shaft tube 689 can attach to the outer shaft tube 682 at a location at side of the shaft tube 682 (such as a location midway along the active tip 681A), and the temperature probe can extend out to the side of the electrode 680 (such as a location lateral to the active tip 681A).

In some embodiments, the temperature-sensor shaft 630 can include a bend near its distal end so that temperature can be measured at a location offset from the longitudinal axis of the electrode 680. For example, the temperature-sensor shaft 630 can be constructed from a super-elastic material, such as nitinol, that is shaped to define a bend. For example, the distal end of the temperature-sensor shaft 630 can be constructed from a spring coil, a spiral cut tube, or a tube with cuts configured to make the tube flexible or semi-flexible, that is shaped to define a bend. The temperature-sensor shaft 630 can be withdrawn into the temperature-sensor lumen 689 during insertion of the electrode 630 into bodily tissue 190, and then extended out from the the temperature-sensor lumen 689 into bodily tissue 190 to provide for off-axis temperature measurement to the side of the electrode active tip. An off-axis temperature-sensor shaft 630 can be used in a side-output electrode-cannula configuration (such as that shown in FIG. 8) to measure a temperature between the cannula active tip 801A and the electrode active tip 881A.

Figure 7:
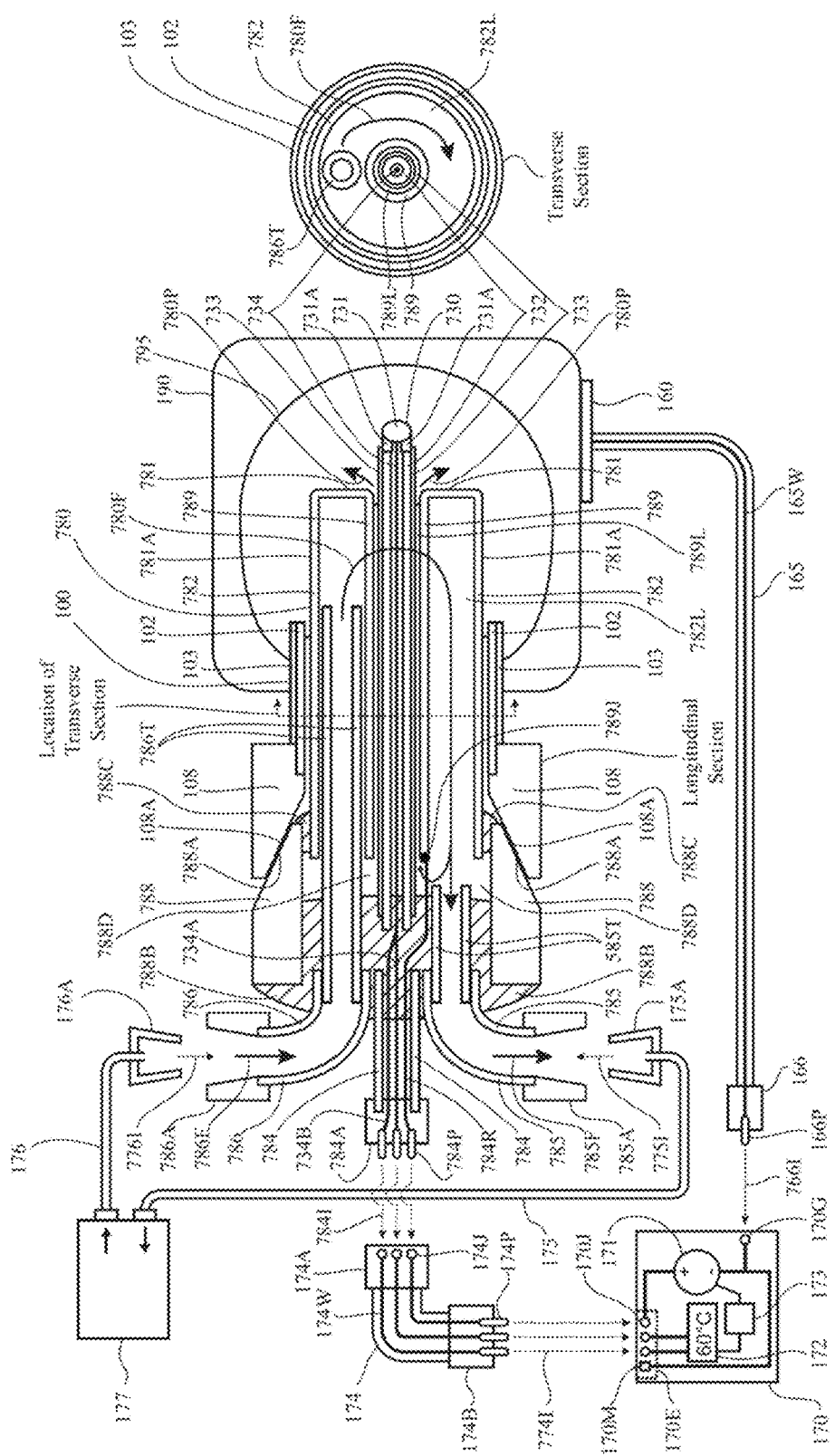
FIG. 7 is a schematic diagram showing a monopolar cooled and perfusion RF ablation system, including electrode 780 which includes channel 789L for outflow of sterile saline coolant from the electrode 780 into bodily issue 190 during RF lesioning, and includes extension temperature sensor assembly 730 that is electrically insulated from the rest of electrode 780 and whose shaft is thermally-insulated, including both the distal aspect of the shaft portion within the electrode and the portion of the shaft portion outside the electrode that is proximal to the temperature, which is in direct contact with bodily tissue.

Referring now to FIG. 7, in accordance with several aspects of the present invention, FIG. 7 presents schematically several embodiments of a monopolar cooled perfusion RF ablation probe system including internal cooling 780F of the electrode 780, coolant perfusion 780P from the electrode 780 into bodily tissue 190, and a coaxial satellite temperature sensor 731 configured to measure tissue temperature at a location distal to active tip 781A by direct contact between the temperature sensor 731 and tissue 190, without directly heating the tissue 190, and with reduced cooling of the temperature sensor 731 through the temperature sensor extension shaft 732. Each of the electrode 780, cannula 100, generator 170, cable 174, cable 784, cable 165, tubing connection 175A, and tubing connection 176A are shown in a cross-sectional view; the cable and tubing connections are exploded for clarity, with the connections indicated by dotted arrows 7741, 7841, 7751, 7761, 7661; and the location of the transverse cross section ("Transverse Section") of the assembled electrode 780 and cannula 100 is indicated in the longitudinal cross-section ("Longitudinal Section") by the line labeled "Location of the Transverse Section". In some embodiments, the electrode 780 can have components, construction methods, dimensions and materials that are the same or similar to those of electrode 180, except as otherwise described herein.

Electrode 780 is inserted into bodily tissue 190 through fully-insulated cannula 100. Via tubes 786, 786T, 785T, and 785, and via hub lumen 788D, coolant pump 177 circulates coolant fluid through the shaft lumen 782L which is bounded by conductive outer shaft tube 782, flat distal plate 781, inner shaft tube 789. Shaft lumen 782L is openly connected to hub lumen 788D, which is bounded by hub outer wall 788, distal rigid hub glue 788C that forms a fluid-tight bond between hub 788 and shaft tube 782, and proximal rigid hub glue 788B that rigidly anchors and electrically-insulates hub body 788, TC shaft 732, cable 784, tubes 785, 786, 785T and 786T. Hub lumen 788D and shaft lumen 782L are openly connected to lumen 789L of electrode shaft inner tube 789, through in which temperature probe 730 is positioned, and which is open to tissue outside and distal to the electrode 780. As indicated by bifurcated arrow 780F, fluid coolant entering the distal electrode fluid lumen 782L from tube 786T flows proximally through lumen 782L to hub lumen 788D, and out from the electrode through two paths: the first path being through tubes 786T and 786, and the second path being through gap 789L between the inner wall of inner electrode shaft tube 789 and the outer electrical insulation 733 covering the thermocouple shaft 730. Due to the relatively small dimension of gap 789L, which can have radial dimension of between 0.00025 and 0.002 inches in some embodiments, as compared with the cross-sectional area of outflow tube 785T, a relatively small portion of the coolant fluid exists through the distal opening of the lumen within tube 789. In some embodiments, the radial dimension of gap 789L can be less than 0.00025 inches. In some embodiments, the radial dimension of gap 789L can be greater than 0.002 inches. One advantage of perfusion of fluid coolant, such as sterile saline or water, from the center of the distal end of the active tip 781A is that coolant is perfused to the region of maximum tissue temperature around the active tip 781A, thereby reducing the maximum tissue temperature, providing for increased RF output delivery to the tissue, and providing for larger lesion size. Use of an coolant that is an ionic fluid, such as saline, has the additional advantage of reducing tissue conductivity near the active tip 781A and thereby shifting ohmic losses and tissue heating away from the active tip 781A and enlarging the size of lesion 795. One advantage of gap 789L as a flow path for tissue perfusion is that fluid exits the active tip 781A at the center of the distal face 781 of the active tip 781A. One advantage of gap 789L as a flow path for tissue perfusion is that the gap thickness can be adjusted to control the rate of tissue perfusion 780P. The distance between the thermocouple 731 and distal open of gap 789L can be adjusted to position thermocouple 731 at a position that achieves stable, robust lesion size control for the flow rate of perfusion 780P (such as the likely location of the maximum tissue temperature during cooled-perfusion RF ablation). In some embodiments, holes can be added through the walls of outer electrode shaft tube 782 and electrode shaft distal end 781 to perfuse coolant into tissue 190; this has the advantage of spreading perfusion around the active tip.

The active tip 781A is the portion of conductive outer shaft 782 that can contact bodily tissue 190, and is the portion of shaft 782 that extends distal to the insulated cannula shaft 102, 103. The RF output signal "+" from RF supply 171 is conducted to the active tip 781A by an insulated wire within cable 174, electrode leader cable wire 784R, conductive junction 789J, and conductive inner electrode tube shaft 789. Extension temperature probe 730 includes stainless steel tubular shaft 732, electrical insulation 733 covering a length of shaft 732 proximal to thermocouple temperature sensor 731, thermocouple junction 731 between the two thermocouple wires of insulated thermocouple bifilar 743, thermally-insulating gasket 731A, and thermocouple bifilar 743 (which in some embodiments, can be one of a variety of insulated two-wire leads, such as a copper-constantan pair, that are known to those skilled in the art of thermocouples). The thermocouple 731 is a ball weld between the electrically-insulated copper wire and the electrically-insulated constantan wire of thermocouple bifilar that passes through plastic thermally-insulative and electrically-insulative gasket 731A (which can be a plastic ring or a glue joint, in some embodiments) and then through stainless-steel temperature-sensor shaft tube 732, before splitting into an insulated copper branch 734B and an insulated constantan branch 734A for independent conduction through cables 784 and 174 to temperature circuit 172 of generator 180. Thermocouple weld 731, gasket 731A, and shaft tube 732 are fixedly joined together to form a continuous, fluid-tight thermocouple-sensor shaft 730. One advantage of thermocouple-sensor shaft 730 is that thermally-insulative gasket 731A provides for spatial precision in sensing of the temperature of tissue in contact with temperature sensor 731 by limiting preferentially heat conduction along the metallic thermally-conductive thermocouple-sensor shaft tube 732 between the temperature sensor 731 and cooled parts of the electrode 780 and tissue having a high temperature gradient near the electrode surface. Cable 174 connects the generator temperature measurement circuit and display 172 to the thermocouple junction 731 via the electrically-insulated wires and pins of leader cable 784. The position of temperature probe 730 is fixed relative to the electrode active tip 781A by rigid hub glue 788B. Temperature probe shaft insulation 733 electrically insulates the temperature probe 730 from the electrode inner shaft tube 789, thereby limiting RF current flow from the temperature probe 730 into tissue 190 and limiting direct RF heating of tissue 190 by probe 730. Probe shaft 732 is separated from coolant flow within lumen 789L by electrical insulation 733, which can be selected to have reduced thermal conductivity. Thermocouple sensor 731 directly contacts tissue 190 with any intervening material to ensure an accurate and rapidly-responding temperature reading. In this example, the generator 170 registers a temperature of 60° C. measured by thermocouple 731 and display on display 172. In some embodiments, shaft tube 132 can be electrically insulative itself (such as a stiff plastic tube), and the shaft electrical insulation 733 can be omitted. In some embodiments, shaft tube 132 can be electrically insulative and thermally insulative (such as a stiff plastic tube), the temperature sensor 731 and the shaft tube 132 can be directly bonded (for example with glue), and both the shaft electrical insulation 733 and the gasket 731A can be omitted. In each of these modified embodiments, and in the embodiment of 730 as shown in FIG. 7, the temperature sensor is in direct contact with bodily tissue, the temperature-sensor shaft 730 does not deliver RF current from RF generator supply 171 to bodily tissue 190, and the temperature-sensor shaft includes a shaft portion proximal to the temperature sensor that thermally-insulates the temperature sensor from heat conduction along the temperature-sensor shaft to the cooled electrode shaft. In some embodiments, temperature-sensor shaft 730 (or any of these modified embodiments) and the associated wiring within the electrode 780 can be replaced by a temperature-sensor shaft like 130, 230, or 630 and the associated wiring within the electrode 180, 280, or 680, respectively.

Figure 8A:
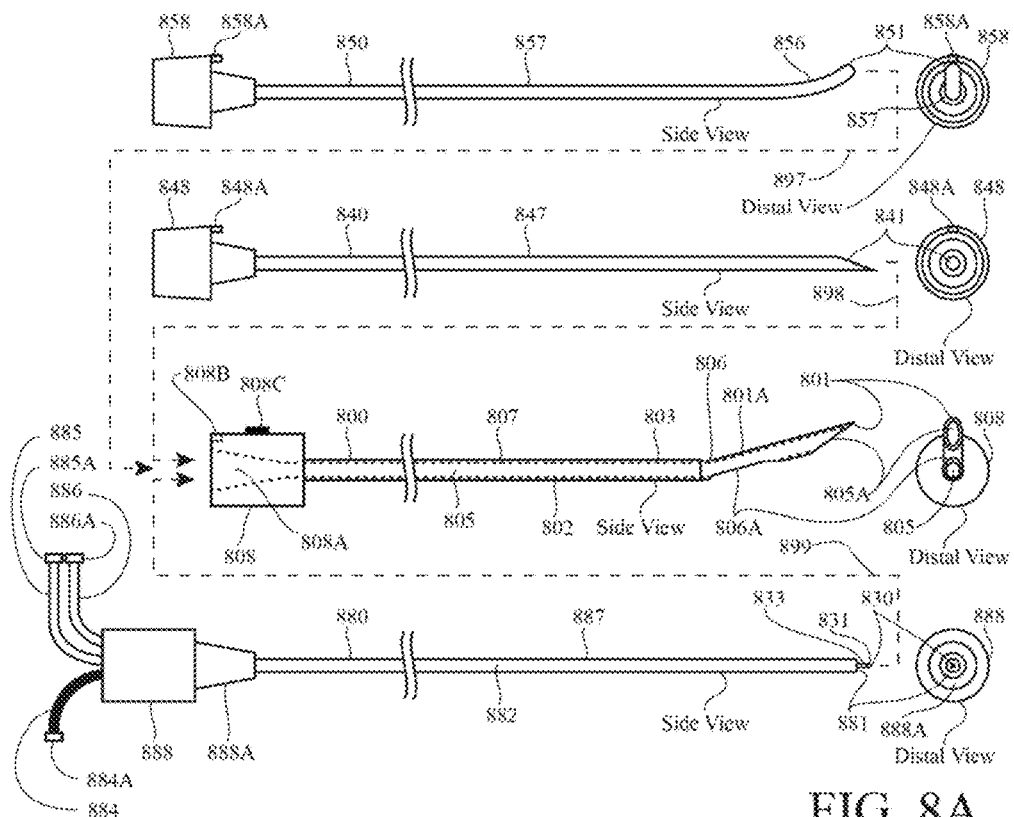
FIG. 8A is a schematic diagram showing a monopolar, side-outlet, cooled RF ablation system including electrode 880 and bent-tip cannula 800, wherein electrode 880 includes a straight shaft 887 that consistently protrudes from side opening 806A of bent-tip cannula 800 when fully inserted into cannula 800 through the cannula proximal hub port 808A irrespective of the rotational orientation of electrode 880 about the longitudinal axis of its shaft relative to the cannula, wherein electrode 880 includes which includes a distal extension temperature sensor 831, and wherein the cannula active tip 801A is electrified by the electrode shaft 882 when the electrode is inserted into cannula 800 through the cannula proximal hub port 808A.
Figure 8B:
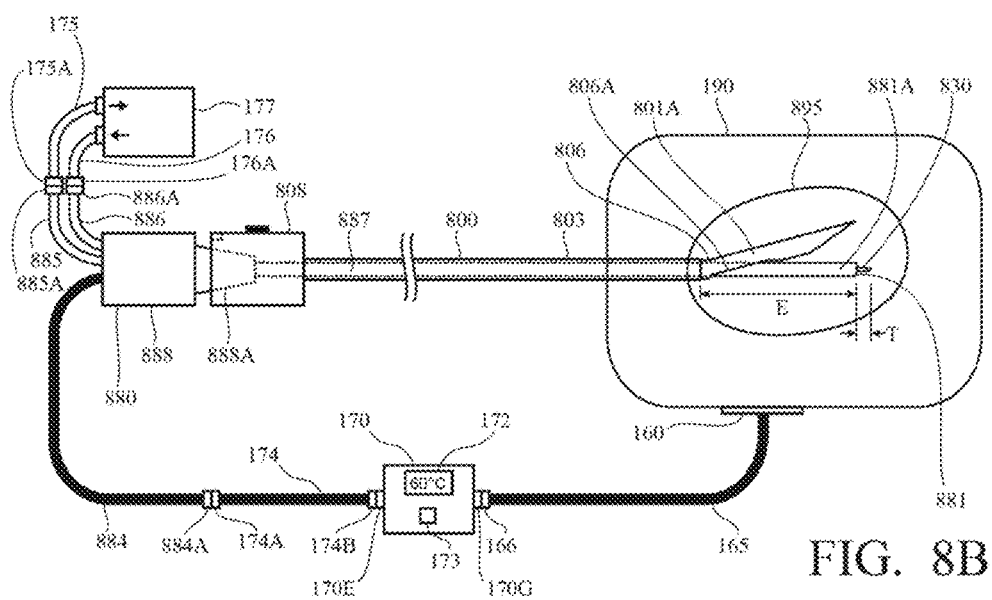
FIG. 8B is a schematic diagram showing the operation of the cooled RF system of FIG. 8A wherein an RF ablation zone 895 is created in bodily tissue around the assembly of the cannula active tip 801A and the portion of the electrode shaft 881A extending from the side opening 806 in the cannula active tip 801A, and a temperature distal to the electrode active tip 881A is measured by extension temperature sensor 831 and controlled by generator 170.

Referring now to FIG. 8, in accordance with several aspects of the present invention, FIG. 8 refers collectively to FIG. 8A and FIG. 8B. FIG. 8 and presents schematically several embodiments of a cooled RF ablation probe system including cannula 800 having an insulated shaft 803 and an active tip 801A at its distal tissue-piercing end, a cannula stylet 850 including a shaft bend 856 that allows the stylet 850 to be directed past cannula side opening 806A into the cannula lumen 805 distal to the side opening 806A, an internally-cooled RF electrode 880 which electrifies the cannula active tip 801A and whose blunt distal end 881 consistently extends out from a side opening 806A near the cannula tissue-penetrating end 801 when the straight electrode shaft 887 is fully inserted into the cannula lumen 805 through the cannula hub 808, and a straight extension stylet 840 having a straight shaft 847 that extends out from the cannula side opening 806A to create a path in bodily tissue for later insertion of the straight electrode shaft 887 via the cannula side opening 806A. The electrode 880 is identical to the electrode 180 shown in FIG. 1. The shaft 847 of the extension stylet 840 is sized relative to the stylet cap 848 so that the extension stylet extends beyond the cannula side opening 806A by the same length as does the electrode shaft 880 when fully inserted into the cannula lumen 805 via the cannula hub 808. The extension stylet 840 is configured to consistently extend from the cannula side opening 806A when the extension stylet 840 is fully inserted into the cannula lumen 805 via the cannula hub 808. In one aspect, FIG. 8 relates to the use of a non-tissue-piercing cooled RF electrode 880 having a straight shaft and distal extension temperature sensor shaft 830 in concert with an RF cannula 800 to enlarge the size of an RF heat lesions both by internally-cooling of the electrode shaft 887 and increasing the effective active tip surface (comprising both the cannula active tip 801A and the extension of the electrode shaft 882 from the cannula side outlet 806A) by means of a side-outlet electrode configuration. Stylet hub tab 858A and cannula hub slot 808B engage to help the user orient the bend 856 of stylet shaft 857 toward the bend 806 of cannula shaft 807. In one aspect, FIG. 8 relates to the use of a cooled RF electrode 880 having a straight shaft and distal extension temperature sensor shaft 830 in concert with an side-outlet RF cannula 800 to enlarge the size of, and control of, RF heat lesions, by internally-cooling of the electrode shaft 887, by controlling a tissue temperature measured accurately and rapidly at a distance from the combined electrode-cannula RF probe, and by increasing the effective active tip surface area (comprising both the cannula active tip 801A and the extension of the electrode shaft 882 from the cannula side outlet 806A) by means of a side-outlet electrode configuration. In one aspect, FIG. 8 relates to an electrode 880 that consistently protrudes from the side outlet 806A in the side wall of a cannula shaft 807 if the electrode 880 is fully inserted through the cannula lumen 805 in any user-selected rotational orientation about the longitudinal axis of the electrode shaft 887, and in any rotational orientation about longitudinal axis of the electrode shaft 887 for which cables 884 and 174 (and tubes 885, 886, 175, 176, if applicable) attached to the electrode 880 do not exert substantial torque on the electrode 880 or cannula 800, nor sufficient torque on the electrode 880 or cannula 800 to rotate or displace the electrode 880 or cannula 800 from their positions within bodily tissue 190, even in the absence of additional mechanical support or constraint of the electrode 880 or cannula 800.

The electrode 880 includes a flat distal point 881, coolant inflow tube 886 with connector 886A, and coolant outflow tube 885 with connector 885A, and generator connection wire 884 with connector 884A, which is connected to generator 180 via extension cable 174. Coolant pumped by coolant pump and source 177 through tube 886 flows to the distal end 881 of the electrode shaft 882, then reverses direction to flow back to the proximal hub 888 and out through the tube 885. RF signals applied through cable 174 and connector 884A are conducted through cable 884 to the conductive electrode shaft 882 outer surface. Temperature signals measured at the electrode distal end 831 are conducted through cable 884 to connector 884A and cable 174 from which the signals can be measured by an RF generator 170. The shaft 882 of the electrode 880 is stiff to provide for penetration of solid tissue 190. In this embodiment, the distal tip 881 is blunt. In this embodiment, the distal tip includes a coaxial extension 830 that holds a temperature sensor 831 at a distance from the conductive shaft 882, wherein the extension is electrically insulated from the shaft 882, and wherein the extension is fixed to the shaft 882. In some modified embodiments, the distal tip 881 can include a coaxial or lateral extension that holds a temperature sensor at a distance from the conductive shaft 882, wherein the extension can be either electrical connected to the shaft 882 or electrically insulated from the shaft, and wherein the extension can either be fixed to the shaft 882 or movable relative to the shaft 882 (such as in the example of electrode 680 in FIG. 6). The cannula bend 806 and side opening 806A are configured so that the electrode shaft 887 will not enter the distal portion of the lumen 805 within the cannula active tip 801A when the electrode is inserted into the cannula lumen 805 through the cannula hub 801 in any rotational orientation. In some embodiments, the electrode 880 and cannula 800 can have dimensions in the same ranges as those possible for embodiments of the electrode 180 and the cannula 100. For some tissue ablation applications in large organs such as the liver, the electrode shaft 882 can be 17 gauge and the cannula shaft 802 can be 15 gauge. In some embodiments, the electrode 880, cannula 800, and stylet 840 can have the same general features and dimensions of the electrode 180, cannula 100, and stylet 140.

In one aspect, FIG. 8 relates to a cannula 800 having an active tip 801A and a bend 806 in the cannula shaft 807, and an internally-cooled RF electrode 880 having a substantially straight shaft 887 that electrifies the cannula active tip 801A and extends from a side opening 806 near the cannula tissue-penetrating end 801, wherein the assembly of the electrode 880 and the cannula 800 can be used to generate a large, asymmetrical heat lesion around both the cannula active tip 801A and the portion of the electrode shaft 881A that extends out of the cannula side opening 806, wherein heat lesion formation is controlled using the temperature measured by temperature sensor 831 at the distal end of extension tip 830, and wherein the extension temperature sensor 831 is physically, thermally, and electrically separated from coolant within electrode shaft tube 882. In one aspect, FIG. 8 relates to the adaptation of an internally-cooled RF electrode having a stiff, straight shaft and distal satellite temperature sensor 831, to a side-opening RF ablation configuration.

Referring now to FIG. 8A, the electrode 880, cannula 800, stylet 850, and extension stylet 840 are shown separately in both an external side view of their longitudinal axes ("Side View") and in a view from their distal ends ("Distal View").

Referring now to FIG. 8B, the electrode 880 and cannula 800 are shown in assembled configuration, producing an RF heat lesion 895 within bodily tissue 190 using monopolar RF, internal electrode cooling, side-outlet-tip, and distal satellite temperature control methods at the same time. The pump and coolant source 177 cools the electrode shaft 882. The generator 170 electrifies the electrode shaft 882 and the cannula active tip 801A with an RF signal. The ground pad 160 carries return current from the electrode shaft 882 and the cannula active tip 801A. This configuration was achieved by the process of inserting the cannula 800 into the tissue 190 with the stylet 850 fully inserted into the cannula lumen 805, removing the stylet 850 from the cannula 800, piercing extension stylet 840 into the tissue 190 through cannula lumen 805 and out from cannula side opening 806 in order to create a path through the tissue 190 for electrode 880, removing the stylet 840 from the cannula 800, inserting the electrode 880 into the cannula lumen 805 via the cannula hub 808, connecting the electrode 880 to the pump 177 and RF generator 170, connecting the RF generator 170 to one or more ground pads 160 placed on the surface of bodily tissue 190, circulating cooling fluid such as saline or water through the electrode shaft 882 by means of the pump 177, and applying an RF potential between the electrode shaft 882 and the ground pad 160 by means of the RF generator 170. RF current flows into tissue 190 from both the extension of the electrode shaft out of the cannula side opening 881A and the cannula active tip 801A, due to conduction of RF current between the electrode conductive shaft 882 and conductive inner wall of the cannula conductive shaft tube 802.

Rotating an electrode that is attached to a cable (for example, electrode 880 and leader cable 884; or electrode 880 and the assembly of cables 884 and 174 in FIG. 8; or electrode 880 and coolant-pump-tube cables 175, 176, 885, and 886), or rotating a cable in order to attach it an electrode (for example, generator extension cable 174 attached to electrode 880), can twist the cable and thereby store mechanical energy in the cable like a torsion spring, so that the cable and attached electrode exert a torque in the direction opposite the direction of the twist. For example, rotating an electrode around the long axis of its shaft (eg shaft 887 of electrode 880) can twist an attached cable (eg leader cable 884 of electrode 880) about and along the length of the cable due to, for example, the cable being attached to a generator at its other end (eg cable 174 attached by connector 174B to generator 170 in FIG. 8), the cable being connected to a coolant pump at its other end (eg cables 885 and 886 attached to pump 177 in FIG. 8), the cable being constrained at some point along its length (including by other parts of the cable), or the cable simply being weighed down by its own mass. When an electrode attached to a twisted cable is inserted into a cannula (for example, electrode 880 inserted into cannula 800) and the hubs of the electrode and cannula are mechanically coupled (such as by the press fit between a male luer taper 888A and a female luer port 808A), the torque generated by the cable is transferred to the cannula, and the cannula can rotate from a desired position in bodily tissue 190 selected by a physician. Similarly, torque from a twisted cable can rotate the electrode within the cannula lumen, thereby generating rotational motion and reduced "sliding" friction between electrode and cannula that can cause the electrode to slip out of the cannula lumen, or thereby jamming or damaging an electrode having a curved shaft protruding from the cannula side opening. Therefore, for a side-outlet electrode-cannula ablation system wherein the electrode can extend out from an opening in the side wall of a cannula shaft and the electrode is attached to or must be attached to a cable (examples of which are presented in FIGS. 1 through 15 of U.S. application Ser. Nos. 14/520,305 and 14/520,310), it is an advantage that the electrode consistently emerges from the side opening in the cannula wall (eg 806) when the electrode is fully inserted into the cannula lumen (eg 805), irrespective of the rotational orientation of the electrode shaft about the long axis of the cannula shaft (such as is the case for the RF ablation system including straight-shaft electrode 880 and bent-tip side-outlet cannula 800 in FIG. 8 of the present invention, and as is the case for each of the side-outlet electrode-cannula ablation systems presented in FIGS. 1 through 9 of U.S. application Ser. Nos. 14/520,305 and 14/520,310, and is the case for a non-cooled RF electrode having a straight nitinol shaft that extends from a side opening in the active tip of an RF cannula configured for pain management ablation), because this feature allows a physician user to select freely a rotational orientation of the electrode within the cannula lumen that does not substantially twist the electrode cable and, thus, does not perturb the intended orientation of the electrode within the cannula, nor the intended position and orientation of the cannula relative to target anatomy, without compromising the side-outlet operation of the system, and irrespective of the rotational orientation of the cannula about its long axis. Similarly, one disadvantage of a side-output electrode-cannula ablation system for which the electrode can only extend out of the side opening of the cannula shaft if the electrode is in a particular relative rotational orientation (or particular range of relative rotational orientations) about the long electrode-cannula shaft axis (such as in some cases where the electrode shaft that is shaped to define a bend and the electrode can bypass the cannula side opening in some rotational orientations about its long axis) is that rotation of the electrode and an attached cable in order to achieve a special orientation required for the electrode to emerge from the side opening of the cannula already positioned and oriented in bodily tissue, or rotation of a cable to attach the cable to the electrode inserted and oriented within the cannula, can induce torque in the cable, and that torque can inadvertently perturb the position and orientation of the electrode and/or cannula from their desired locations within bodily tissue unless additional monitoring or mechanical support is provided. As such, for some embodiments of side-outlet electrode-cannula ablation systems for which the electrode can only extend out of the cannula side-opening in a particular rotational orientation (or in a particular range of rotational orientations) about the electrode-cannula combined shaft long axis (examples of which are presented in FIGS. 10 through 15 of U.S. application Ser. Nos. 14/520,305 and 14/520,310), the electrode cable can be adapted to include one or more of features selected from the following list: having a very small torsion coefficient, being detachable from and attachable to the electrode by means of a connector that is rotationally symmetric about the longitudinal axis of the electrode, being attached to the electrode by a junction that allows the electrode to rotate about its long axis relative to the cable. Each of these features has the advantage of limiting torque due to cable twisting and, thus, limiting inadvertent rotation of the electrode and/or the cannula from its desired position.

Paragraph 1: A system for tissue ablation including an electrode, the electrode including an elongated electrode shaft having a proximal end and a distal end, and an elongated temperature-sensor shaft having a proximal and a distal end, wherein the outer surface of the electrode shaft includes an electrode active tip that conducts RF current to bodily tissue from an RF generator, the electrode shaft includes a coolant lumen within at least the active tip portion of which fluid coolant circulates, and the electrode shaft includes a temperature-sensor lumen that is physically separated from the coolant lumen within the electrode by a fluid-tight barrier; the temperature-sensor shaft is positioned within the temperature-sensor lumen and the distal end of the temperature-sensor shaft extends out from the temperature-sensor lumen into bodily tissue; the temperature sensor shaft is separated from the temperature-sensor lumen by a gap and a plastic layer along at least the distal portion of the temperature-sensor shaft that is within temperature-sensor lumen; the temperature-sensor shaft does not deliver sufficient RF current from the RF generator to the bodily tissue to substantially heat the bodily tissue; and the temperature-sensor shaft includes a temperature sensor in the portion of the temperature-sensor shaft that extends out of from the temperature-sensor lumen into bodily tissue.

Paragraph 2: The system of Paragraph 1 wherein the temperature sensor forms a portion of the outer surface of the temperature-sensor shaft and directly contacts bodily tissue.

Paragraph 3: The system of Paragraph 2 wherein the temperature sensor forms the distal surface of the temperature-sensor shaft.

Paragraph 4: The system of Paragraph 2 where in the temperature sensor is a thermocouple.

Paragraph 5: The system of Paragraph 1 wherein the temperature sensor is a thermocouple.

Paragraph 6: The system of Paragraph 5 wherein the temperature-sensor shaft includes a stainless steel tube, an insulated constantan wire within the lumen of the stainless steel tube, and the thermocouple is a weld between the stainless steel tube and the constantan of the insulated constantan wire.

Paragraph 7: The system of Paragraph 3 wherein the temperature sensor is rounded to facilitate penetration of bodily tissue.

Paragraph 8: The system of Paragraph 7 wherein the temperature sensor is sharpened to form a tissue-piercing point.

Paragraph 9: The system of Paragraph 8 wherein the distal end point of the electrode shaft is tapered, and the electrode is configured to pierce solid bodily tissue.

Paragraph 10: The system of Paragraph 1 wherein the plastic layer is thermal insulation.

Paragraph 11: The system of Paragraph 1 wherein the plastic layer is electrical insulation.

Paragraph 12: The system of Paragraph 1 wherein the plastic layer is the inner surface of the temperature-sensor lumen.

Paragraph 13: The system of Paragraph 1 wherein the plastic layer is a portion of the outer surface of the temperature-sensor shaft.

Paragraph 14: The system of Paragraph 13 wherein the plastic layer is the outer surface of a portion of the temperature-sensor shaft longitudinally spanning from a first position inside the temperature-sensor lumen to a second position that extends outside the temperature-sensor lumen into bodily tissue and is proximal to the temperature sensor.

Paragraph 15: The system of Paragraph 14 wherein the temperature sensor is a thermocouple that forms the outer surface of the distal point of the temperature-sensor shaft, the plastic layer is electrically insulative, and the thermocouple is electrically insulated from the electrode active tip within the electrode, the RF generator, and cables that connect the electrode and the RF generator.

Paragraph 16: The system of Paragraph 15 wherein the thermocouple is a weld at the end of a stainless steel tube within the temperature-sensor shaft, and the plastic layer is electrical insulation covering the stainless steel tube.

Paragraph 17: The system of Paragraph 14 where the temperature-sensor shaft includes an elongated plastic tube forming its proximal end, and a temperature-sensor forming its distal end.

Paragraph 18: The system of Paragraph 13 wherein the plastic layer is electrical insulation that covers the entire surface of the portion of the temperature-sensor shaft that extends out of the temperature-sensor lumen into bodily tissue.

Paragraph 19: The system of Paragraph 18 wherein the temperature sensor shaft conducts the RF current from the RF generator to the electrode active tip.

Paragraph 20: The system of Paragraph 1 wherein the temperature-sensor shaft extends out from the distal end of the electrode shaft tube into bodily tissue.

Paragraph 21: The system of Paragraph 1 wherein the temperature-sensor shaft extends out from a side of the electrode shaft tube into bodily tissue.

Paragraph 22: The system of Paragraph 1 wherein the temperature-sensor shaft extends out from the electrode active tip.

Paragraph 23: The system of Paragraph 1 wherein the portion of the temperature-sensor shaft that extends out from the temperature-sensor lumen into bodily tissue is substantially straight.

Paragraph 24: The system of Paragraph 1 wherein the portion of the temperature-sensor shaft that extends out from the temperature-sensor lumen into bodily tissue is shaped to define a bend.

Paragraph 25: The system of Paragraph 1 wherein the electrode active tip includes the distal end of the electrode shaft.

Paragraph 26: The system of Paragraph 25 wherein the temperature-sensor shaft extends out from the distal end surface of the electrode active tip.

Paragraph 27: The system of Paragraph 25 wherein the distal end point of the electrode shaft is substantially flat.

Paragraph 28: The system of Paragraph 25 wherein the distal end point of the electrode shaft is tapered.

Paragraph 29: Then system of Paragraph 25 wherein the coolant lumen has substantially constant wall thickness to the exterior of the electrode at the distal end of the electrode shaft.

Paragraph 30: The system of Paragraph 1 wherein the electrode active tip is proximal to a non-conductive outer surface of the distal end of the electrode shaft.

Paragraph 31: The system of Paragraph 1 wherein electrical insulation covers the proximal end of the electrode shaft to define the electrode active tip at the distal end of the electrode shaft.

Paragraph 32: The system of Paragraph 1 wherein the electrode active tip is the portion of the electrode shaft that extends into bodily tissue from the distal end of a cannula which includes an electrically-insulated shaft through which the electrode is inserted.

Paragraph 33: The system of Paragraph 1 wherein the electrode is inserted into bodily tissue through a cannula, the cannula having an elongated cannula shaft, the cannula shaft having a distal end and a proximal end, the cannula shaft having an electrically insulated proximal end and an electrically conductive cannula active tip at the cannula shaft distal end.

Paragraph 34: The system of Paragraph 33 wherein the cannula active tip is electrified by physical contact with the electrode active tip and delivers RF current to the bodily tissue.

Paragraph 35: The system of Paragraph 33 wherein the electrode active tip does not extend distal to the cannula distal end.

Paragraph 36: The system of Paragraph 33 wherein the electrode active tip is the portion of the electrode shaft that extends into bodily tissue from a side opening in a side of the cannula shaft, the cannula active tip is electrified by physical contact with the electrode shaft and delivers RF current to the bodily tissue.

Paragraph 37: The system of Paragraph 36 wherein the electrode shaft extends from the side opening into bodily tissue irrespective of the rotational orientation of the electrode shaft about its long axis relative to the cannula shaft.

Paragraph 38: The system of Paragraph 36 wherein the electrode is attached to a cable connected to an RF generator, the user can freely select the rotational orientation of the electrode relative to the cannula such that the electrode and cable do not exert force or torque sufficient to displace or rotate the cannula from its position within bodily tissue.

Paragraph 39: The system of Paragraph 33 wherein electrode-shaft electrical insulation covers the proximal end of the electrode shaft to define the electrode active tip at the distal end of the electrode shaft, the electrode active tip and a distal portion of the electrode-shaft electrical insulation extends out of the cannula into bodily tissue, and cannula active tip is connected to a different electrical potential than is connected to the electrode active tip, and the RF current flows through bodily tissue between the cannula active tip and the electrode active tip.

Paragraph 40: The system of Paragraph 39 wherein the electrode conducts the electrical potential connected to the cannula active tip from the RF generator.

Paragraph 41: The system of Paragraph 39 wherein the electrical potential connected to the cannula active tip is conducted from the RF generator via physical contact of a first conductive element included in the electrode and a second conductive element included in the cannula.

Paragraph 42: The system of Paragraph 39 wherein the electrode and cannula include MRI-safe materials and metals that limit heating by MRI magnetic fields, forces induced by MRI magnetic fields, and distortion in an MRI image of bodily tissue in which the electrode and cannula are inserted.

Paragraph 43: The system of Paragraph 1 wherein the electrode shaft includes a second electrode-reference active tip, and electrical insulation covering the proximal end of the electrode shaft and separating the electrode active tip from the electrode-reference active tip; wherein the electrode-reference active tip is connected to a different electrical potential than is connected to the electrode active tip, and the RF current flows through bodily tissue between the electrode-reference active tip and the electrode active tip.

Paragraph 44: The system of Paragraph 1 wherein the temperature-sensor shaft is rigidly attached to the electrode shaft.

Paragraph 45: The system of Paragraph 1 and additionally including an electrode hub attached to the proximal end of the electrode shaft, wherein the temperature-sensor shaft is rigidly fixed to the electrode hub.

Paragraph 46: The system of Paragraph 1 wherein the temperature-sensor shaft can slide relative to the electrode shaft.

Paragraph 47: The system of Paragraph 46 where the distal end of the temperature-sensor shaft is shaped to define a bend.

Paragraph 48: The system of Paragraph 1 wherein the gap spans substantially the entire length of the electrode shaft.

Paragraph 49: The system of Paragraph 1 wherein the thermally-insulative layer spans substantially the entire length of the electrode shaft.

Paragraph 50: The system of Paragraph 1 wherein the electrode shaft is stiff.

Paragraph 51: The system of Paragraph 1 wherein the outer surface of the electrode shaft a metallic tube.

Paragraph 52: The system of Paragraph 1 wherein the electrode is configured for insertion into solid tissue.

Paragraph 53: The system of Paragraph 1 wherein the fluid-tight barrier is a metallic barrier.

Paragraph 54: The system of Paragraph 53 wherein the coolant lumen is configured to contain high pressure fluid coolant.

Paragraph 55: The system of Paragraph 1 wherein the electrode perfuses fluid into the bodily tissue near the electrode active tip.

Each of the internally-cooled electrodes 180, 380A, 380B, 380C, 380D, 480, 680, 780, 880 advantageously reduce measurement bias and delay in sensing a temperature distal to the active tip (eg 181A) of the internally-cooled electrode (eg 180) by providing a rigid support structure with minimal thermal mass (eg 132) for reliable and robust positioning of a temperate sensor (eg 131) in solid bodily tissue 190; positioning the temperature sensor (eg 131) in direct contact with the tissue 190 without intervening material; providing thermal insulation (eg 133) and a physical gap (189L) over the length of the electrode shaft (eg 187) between the support structure (eg 132) of the temperature sensor (eg 131) and coolant flowing (eg 180F) within the electrode shaft (eg 187); providing thermal insulation (eg 133) over the length of temperature-sensor shaft (eg 130) extending out of the electrode shaft and proximal to the temperature sensor (eg 131); and electrically isolating the temperature sensor (eg 131) from RF potentials (eg generated by RF supply 171). In some embodiments of electrodes 180, 280, 380A, 380B, 380C, 380D, 480, 680, 780, 880, the thermocouple temperature sensor (eg 131, 731) can be replaced by another type of temperature sensor, such as a thermistor or fiber-optic temperature sensor. Reducing bias and delay in satellite temperature measurement for control of cooled RF lesioning had advantages that include: improving lesion size reproducibility; allowing for higher set temperatures and thus larger lesion sizes with reduce risk of the maximum tissue temperature exceeding a desired limit (such as boiling) or excessive lesion size formation due to misregistration between the temperature sensor location and the maximum temperature of heated tissue; allowing for larger cooled RF heat lesions in nervous tissue near sensitive structures such as the skin surface and nerves whose function it is desired to preserve; and reducing complications due to lesion size variability.

Internally-cooled electrode 580 advantageously simplifies manufacturing by conducting both the RF potential delivered to the active tip 581A and one of the wires 584T for the thermocouple temperature sensor 531 through the same cable wire 584T, and advantageously reduces measurement bias in sensing a temperature distal to the active tip 581A of the internally-cooled electrode 580 by providing a rigid support structure 532 having minimal thermal mass for reliable and robust positioning of a temperate sensor 531 in solid bodily tissue 190; positioning the temperature sensor 531 in close contact with the tissue 190, with only a thin layer of electrical insulation 533 intervening; providing thermal insulation 533 and a physical gap 589L over the distal length of the electrode shaft 587 between the support structure 532 of the temperature sensor 531 and coolant flowing 580F within the electrode shaft 587; and preventing the temperature sensor 531 from conducting RF current from the RF supply 171 to bodily tissue 190.

Each of the internally-cooled electrodes 180, 280, 380C, 380D, 480, 580, 680, 780, 880 advantageously reduces the maximum tissue temperature and delays the initial tissue boiling that typically occurs distal to the electrode active tip and can limit heat lesion size, by means of including a substantially flat distal end (eg 181) to reduce electric field strength near the active tip along the central axis of the active tip (eg 181A), and by means of including a thin, relatively uniform wall thickness over the entire active tip (eg 181) including its flat distal face (eg 181A) in order to enhance tissue cooling distal to the electrode active tip (eg 181A).

For all electrodes, cannula, stylets, shafts, and elongated probes referred to herein, the distal end of a probe is means end of the elongated structure of the probe that is configured to be first inserted into bodily tissue, and the proximal end of electrode 180 means the opposite end of the elongated probe structure. In some embodiments, the distal end of a probe is configured to penetrate or pierce the bodily tissue, and the proximal end is configured to be manipulated or connected to structures outside the bodily tissue. For all electrodes, cannula, stylets, shafts, and elongated probes referred to herein, a more distal structure of the probe is closer to the distal end of the probe, and a more proximal structure of the probe is closer to the proximal end of the probe.

In some embodiments, each of the cannulas, electrodes, stylets, and cables presented in FIG. 1 through 8 can be disposable (eg sterile packed and single use only) or reusable (eg autoclavable). In some embodiments, each of the cannulas, electrodes, and stylets presented in FIG. 1 through 8 can have a different construction that still provides the key functional and operational features of the present invention; for example, the fully-electrically-insulated shaft 107 of cannula 100 can be constructed from an elongated electrically-insulative tube, rather than by covering an electrically-conductive tube 102 with electrical insulation 103; for example, the shaft of cannula 300A can be constructed either from an elongated electrically-insulative tube at whose distal end is mounted a conductive active tip tube 301AA, or by covering the proximal portion 303A of an electrically-conductive tube with electrical insulation 303A to define an active tip 301AA; for example, different lengths of the electrode shaft 187 can be constructed by stacking different tubular pieces having different physical characteristics; for example, the active tip of a probe (eg a cannula or electrode) can be constructed from a conductive ring covering the probe shaft; for example, the bipolar RF probe assembly of FIG. 2B can constructed as a single unitized electrode having multiple active tips, for example by axially fusing alternating tubes of electrically-conductive material (forming the active tips) and electrically-insulating material, or by reducing the radius of each of multiple electrically-conductive rings (eg by swaging) over an electrically-insulative shaft tube. In some embodiments, each of the electrodes or cannulas presented in FIG. 1 through 8 can be adapted to include more than one conductive active tip. In some embodiments, each of the ablation systems presented in FIG. 1 through 8 can be adapted to deliver one or more forms of electrical signals selected from the list: direct current, alternating current, radiofrequency, a combination of radiofrequency and direct current, microwave, stimulation, nerve stimulation, muscle, low frequency, high frequency, and combinations thereof. In some embodiments, each of the electrodes presented in FIG. 1 through 8 can be adapted for either temperature-controlled ablation, temperature-monitoring ablation, or non-temperature-controlled ablation. In some embodiments, each of the electrodes and cannula presented in FIG. 1 through 8 can be adapted to include electrical insulation covering a part of the electrode conductive shaft, and the assembly of the cannula and electrode can operate as a bipolar ablation probe system. In some embodiments, each of the systems presented in FIG. 1 through 8 can be adapted for application of monopolar signals, bipolar signals, multi-polar signals, and combinations and sequences thereof, either in concert with other physically-separate probes, or by means of multiple separate electrode contacts included on a single probe shaft. In some embodiments, each of the cannulae presented in FIG. 1 through 8 can be adapted so that its cannula shaft is completely electrically insulated and an extension of an electrode out through an opening of the cannula lumen solely conducts electricity to bodily tissue. In some embodiments, each of the cannulae presented in FIG. 1 through 8 can be adapted so that the cannula active tip is positioned at a position along its shaft that is not at the most distal point of the cannula shaft. In some embodiments, each of the electrodes presented in FIG. 1 through 8 can be adapted so that more than one length of the electrode shaft is covered by electrical insulation to form an active tip not at the most distal point of the electrode shaft. In some embodiments, each of the bipolar electrode and cannula assemblies presented in FIG. 1 through 8 can be adapted for a two-active-tip monopolar operation wherein both the electrode active tip and the cannula active tip are connected to the same electrical potential and referenced to a common reference electrode, such as a ground pad. In some embodiments, each of the bipolar electrode and cannula assemblies presented in FIG. 1 through 8 can be adapted for a two-active-tip monopolar-bipolar operation wherein the active tip of the electrode is connected to a first electrical potential, the active tip of the cannula is connected to a second electrical potential, and a reference electrode is connected to a third electrical potential, and the electrode active tip, the cannula active tip, and a reference electrode are all applied to the same bodily tissue. In some embodiments, each of the systems presented in FIG. 1 through 8 can be adapted for tissue ablation in one or more of a wide variety of clinical contexts including tissue coagulation, pain management, tumor ablation, cardiac ablation, tissue devascularization, open surgical procedures, percutaneous surgical procedures, laparoscopic surgical procedures, facet denervation, SIJ denervation, pulsed RF neuromodulation, pulsed RF lesioning, preparation of collapsed bone for injection of bone cement, electrocautery of intravertebral nerves, thermocoagulation of intra-bone structures. In some embodiments, each of the systems presented in FIG. 1 through 8 can be adapted for tissue ablation in any one or more parts of the human body, including the spine, bone, spinal nerve, peripheral nerve, knee nerve, hip nerve, shoulder nerve, foot nerve, hand nerve, carpel tunnel, sympathetic nerve, trigeminal nerve, medial branch nerve, sacral lateral branch nerve, brain, heart, liver, kidney, lung, pancreas, prostate, adrenal gland, thyroid, gall bladder, vertebral body, intervertevral nerve, basivertebral nerve, an intervertebral disc, nerve in an intervertebral disc, posterior annulus of an intervertebral disc, nucleus of the intervertebral disc, muscle, osteoid osteoma. In some embodiments, the generator 170 can be connected to multiple electrodes and probes and/or multiple ground pads at the same time. In some embodiments, the generator 170 can include more than two output poles. In some embodiments, the generator 170 can additionally produce a nerve-stimulation signal.

A number of embodiments of the invention have been described. Nevertheless, it will be understood that various modifications may be made without departing from the spirit and scope of the invention. Accordingly, other embodiments are within the scope of the following claims.

What is claimed is:

1. A system for tissue ablation including an electrode configured for insertion into bodily tissue, the electrode including an elongated metallic tubular electrode shaft having a proximal end and a distal end, and an elongated temperature-sensor shaft having a proximal and a distal end, wherein the proximal end of the electrode shaft is electrically insulated to define the electrode active tip at the distal end of the electrode shaft; the electrode active tip is configured to conduct RF current to bodily tissue from an RF generator; the electrode shaft includes a coolant lumen at least within the active-tip portion of the electrode shaft; fluid coolant circulates within the coolant lumen; the electrode shaft includes a temperature-sensor lumen that is physically separated from the coolant lumen by a barrier within the electrode; the temperature-sensor shaft is positioned within the temperature-sensor lumen; the distal end of the temperature-sensor shaft is configured to extend out from the temperature-sensor lumen from the distal end of the electrode shaft into bodily tissue; the temperature sensor shaft is not connected to the temperature-sensor lumen at the distal end of the temperature-sensor lumen; the temperature-sensor shaft is configured to not deliver sufficient RF current from the RF generator to the bodily tissue to substantially heat the bodily tissue; the temperature-sensor shaft includes an elongated temperature-sensor-shaft tube, a plastic layer forming the outer surface of a plastic-layer length of the temperature-sensor-shaft tube, at least one temperature-sensor wire within the lumen of the temperature-sensor-shaft tube, and a temperature sensor attached to the at least one temperature-sensor wire and to the temperature sensor-shaft tube; the temperature sensor forms the outer surface of the distal point of the temperature-sensor shaft and is configured to directly contact bodily tissue; and the plastic-layer length spans from a first part of the temperature-sensor shaft inside the temperature-sensor lumen, to a second part of the temperature-sensor shaft that is configured to extend out from the temperature-sensor lumen into bodily tissue and that is proximal to the temperature sensor.

2. The system of claim 1 wherein the temperature-sensor shaft is rigidly fixed to the electrode, wherein the point of fixation is longitudinal spaced from, and proximal to, the distal end of the electrode shaft.

3. The system of claim 2 and further including an electrode hub rigidly fixed to the proximal end of the electrode shaft, wherein the temperature-sensor shaft is rigidly fixed to the electrode hub.

4. The system of claim 3 wherein the hub includes glue that rigidly anchors the temperature-sensor shaft, coolant tubing, and electrode cables to the electrode hub.

5. The system of claim 1 wherein the temperature-sensor shaft can slide relative the electrode shaft.

6. The system of claim 1 wherein the plastic layer is electrical insulation and thermal insulation.

7. The system of claim 1 wherein the barrier is a metal tube.

8. The system of claim 1 wherein the at least one temperature-sensor wire is an electrically-insulated thermocouple bifilar, and the temperature sensor is a thermocouple junction between the two wires of the thermocouple bifilar.

9. The system of claim 1 wherein the temperature-sensor-shaft tube is a stainless-steel tube, the at least one temperature-sensor wire is an electrically-insulated constantan wire, the plastic layer is applied to an external surface of the stainless-steel tube, the temperature sensor is a thermocouple weld between the temperature-sensor-shaft tube and the constantan wire, the thermocouple is electrically insulated from the electrode active tip within the electrode.

10. The system of claim 1 wherein the plastic-layer length includes the entirety of the temperature sensor shaft configured to extend into bodily tissue.

11. The system of claim 1 wherein the distal end of the electrode active tip is substantially flat.

12. The system of claim 1 wherein the distal end of the electrode active tip is tapered, and the distal end of the temperature-sensor shaft is sharpened.

13. The system of claim 1 wherein the temperature-sensor shaft is substantially straight.

14. The system of claim 1 wherein the temperature-sensor shaft includes bend at or near its distal end.

15. The system of claim 1 wherein the electrode shaft is electrically insulated by electrical insulation applied directly the electrode shaft.

16. The system of claim 1 wherein the electrode shaft is electrically insulated by an electrically-insulated cannula through which the electrode is configured to be inserted into bodily tissue.

17. The system of claim 16 wherein the cannula shaft includes an uninsulated conductive cannula active tip portion at this cannula distal end, the electrode shaft is configured to extend out from a side opening through a side of the cannula into bodily tissue, and the electrode electrifies the cannula active tip to the same electrical potential as the electrode active tip.

18. The system of claim 17 wherein the electrode extends out from the side opening through the side of the cannula irrespective of the rotational orientation of the electrode shaft about its long axis relative to the cannula shaft.

19. The system of claim 1 wherein the electrode shaft includes an electrode-reference active tip that is connected to a different electrical potential than is connected to the electrode active tip, the electrode-reference active tip is electrically insulated and spaced apart from the electrode active tip within the electrode, and RF current flows through bodily tissue between the electrode active tip and the electrode-reference active tip.

20. The system of claim 1 wherein the electrode is MRI compatible.

\* \* \* \* \*